United States Patent
Jeffery et al.

(10) Patent No.: US 9,357,329 B2
(45) Date of Patent: May 31, 2016

(54) METHOD TO PROVIDE DYNAMIC CUSTOMIZED SPORTS INSTRUCTION RESPONSIVE TO MOTION OF A MOBILE DEVICE

(71) Applicant: Ai Golf, LLC, Mesa, AZ (US)

(72) Inventors: Mark John Jeffery, Mesa, AZ (US); Robert Sunshin Komorous-King, Berkeley, CA (US)

(73) Assignee: Aquimo, LLC, Mesa, AZ (US)

( * ) Notice: Subject to any disclaimer, the term of this patent is extended or adjusted under 35 U.S.C. 154(b) by 0 days.

(21) Appl. No.: 13/659,774

(22) Filed: Oct. 24, 2012

(65) Prior Publication Data

US 2013/0150121 A1     Jun. 13, 2013

Related U.S. Application Data

(60) Provisional application No. 61/551,388, filed on Oct. 25, 2011, provisional application No. 61/713,813, filed on Oct. 15, 2012.

(51) Int. Cl.
| | |
|---|---|
| *H04M 1/00* | (2006.01) |
| *H04W 4/00* | (2009.01) |
| *H04M 1/725* | (2006.01) |

(52) U.S. Cl.
CPC ............... *H04W 4/00* (2013.01); *H04W 4/003* (2013.01); *H04M 1/72522* (2013.01)

(58) Field of Classification Search
CPC .................................................. H04M 1/72522
USPC ..................... 455/556.1, 42.1, 42.2, 42.3, 39; 473/219, 212
See application file for complete search history.

(56) References Cited

U.S. PATENT DOCUMENTS

| 5,554,033 A | 9/1996 | Bizzi et al. |
| 5,810,598 A | 9/1998 | Wakamoto |

(Continued)

FOREIGN PATENT DOCUMENTS

| CN | 1154661 A | 7/1997 |
| EP | 1810724 A1 | 7/2007 |

(Continued)

OTHER PUBLICATIONS

"Method to Inject User Testimonial Into an Advertising Stream", IP.Com, IPCOM000195733D, May 13, 2010.

(Continued)

*Primary Examiner* — Sanh Phu
(74) *Attorney, Agent, or Firm* — Morgan Law Offices, PLC

(57) ABSTRACT

A family of sports teaching applications that delivers customized lessons driven by the analysis of user body motions where data is captured via the accelerometer and gyroscope in a mobile device, such as a smartphone is provided. Each specific application is designed with motion data models that define proper form for athletes in club sports such as, but not limited to, golf, baseball hitting, hockey, polo, and racquet sports such as, but not limited to, table tennis, squash, badminton and throwing sports like baseball pitching, football, discus, javelin, and shot put, and other sports such as skiing and running. The Invention is also applicable to the customized fitting of sports equipment such as golf clubs, baseball bats, tennis racquets, etc. to athletes unique swing motions and swing speeds, and for multiplayer tournament competitions via the Internet utilizing the swing motion analysis and system described herein.

56 Claims, 14 Drawing Sheets

(56) References Cited

U.S. PATENT DOCUMENTS

| | | | |
|---|---|---|---|
| 5,879,165 A | | 3/1999 | Brunkow et al. |
| 6,013,007 A | * | 1/2000 | Root et al. ............. 482/8 |
| 7,039,589 B2 | | 5/2006 | Whitham |
| 7,107,533 B2 | | 9/2006 | Duncan et al. |
| 7,185,274 B1 | | 2/2007 | Rubin et al. |
| 7,239,842 B2 | | 7/2007 | Nijim |
| 7,451,156 B2 | | 11/2008 | Ornstein et al. |
| 7,587,323 B2 | | 9/2009 | Matz et al. |
| 7,733,366 B2 | | 6/2010 | Beavers et al. |
| 7,789,742 B1 | * | 9/2010 | Murdock et al. ............ 463/3 |
| 7,796,548 B2 | | 9/2010 | Lee |
| 7,806,777 B2 | | 10/2010 | Cheng |
| 7,825,815 B2 | * | 11/2010 | Shears et al. ............ 340/573.1 |
| 7,927,216 B2 | | 4/2011 | Ikeda et al. |
| 7,942,745 B2 | | 5/2011 | Ikeda et al. |
| 8,029,359 B2 | | 10/2011 | Cheng |
| 2002/0019763 A1 | | 2/2002 | Linden et al. |
| 2002/0032906 A1 | | 3/2002 | Grossman |
| 2003/0172052 A1 | | 9/2003 | Crandell et al. |
| 2005/0054457 A1 | | 3/2005 | Eyestone et al. |
| 2005/0113183 A1 | | 5/2005 | Noble |
| 2006/0063980 A1 | | 3/2006 | Hwang et al. |
| 2008/0221979 A1 | | 9/2008 | Engel |
| 2008/0291220 A1 | | 11/2008 | Cheng et al. |
| 2008/0319787 A1 | | 12/2008 | Stivoric et al. |
| 2009/0162827 A1 | | 6/2009 | Benson et al. |
| 2009/0183010 A1 | | 7/2009 | Schnell et al. |
| 2010/0121227 A1 | | 5/2010 | Stirling et al. |
| 2010/0191578 A1 | | 7/2010 | Tran et al. |
| 2010/0304804 A1 | | 12/2010 | Spivack |
| 2011/0190052 A1 | | 8/2011 | Takeda et al. |
| 2011/0190061 A1 | | 8/2011 | Takeda et al. |
| 2012/0050529 A1 | * | 3/2012 | Bentley ............ 348/139 |
| 2013/0265225 A1 | * | 10/2013 | Nasiri et al. ............ 345/156 |

FOREIGN PATENT DOCUMENTS

| | | |
|---|---|---|
| JP | 2004113689 A | 4/2000 |
| JP | 2007229197 | 9/2007 |
| JP | 2010011926 A2 | 1/2010 |
| KP | 2001003645 B1 | 1/2010 |
| KR | 101059258 B1 | 8/2011 |
| WO | 2004056425 A2 | 7/2004 |
| WO | 2005113079 A2 | 12/2005 |
| WO | 2008052605 A1 | 5/2008 |
| WO | 2010056548 A1 | 5/2010 |
| WO | 2011085494 A2 | 7/2011 |

OTHER PUBLICATIONS

"Demo Tool to Display IBM Services Assets and Show the Value of an Asset Leveraged Approach", IP.Com, IPCOM000182369D, Apr. 28, 2009.

"Method for Creating Custom eBooks", IP.Com, IPCOM0001804D, Mar. 9, 2009.

Johnson et al., "Combining Multimedia Presentation Scripts Using Identifiers", IBM Technical Disclosure Bulletin, vol. 37, No. 02A, p. 605, Feb. 1994.

Press Release, "iPING brings 'Fit for Stroke' update to app for iPhone 4 & iPod touch", 2 pages, Aug. 16, 2011.

Press Release, "PING introduces iPhone and iPod putter fitting application", 1 page, Jul. 19, 2011.

Press Release, "PING's new iPING putter app targets consistency for improved putting", 2 pages, Jun. 14, 2011.

Tech Tips and Toys, New iPing Putter App—for iPhone, Jun. 19, 2011 (Retrieved on http://techtipsandtoys.wordpress.com/2011/06/19/new-iping-putter-app-for-iphone.

Search report and office action from the State Intellectual Property Office of China (SIPO), dated Nov. 10, 2015, for Chinese Application No. 201280052082.3.

European Search report and communication from the EPO accompanying the European Search Report, dated Sep. 23, 2015, for European Patent Application No. 12843067.5.

\* cited by examiner

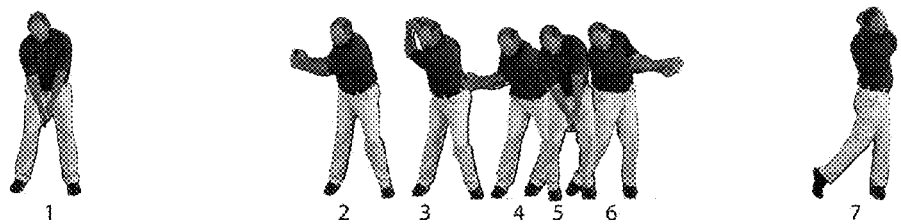
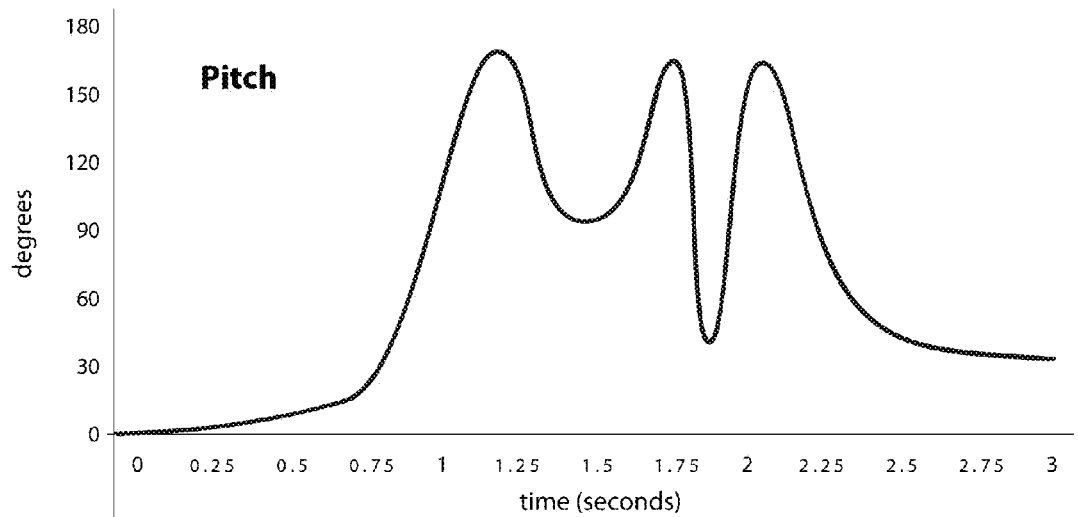
FIG. 10(a)
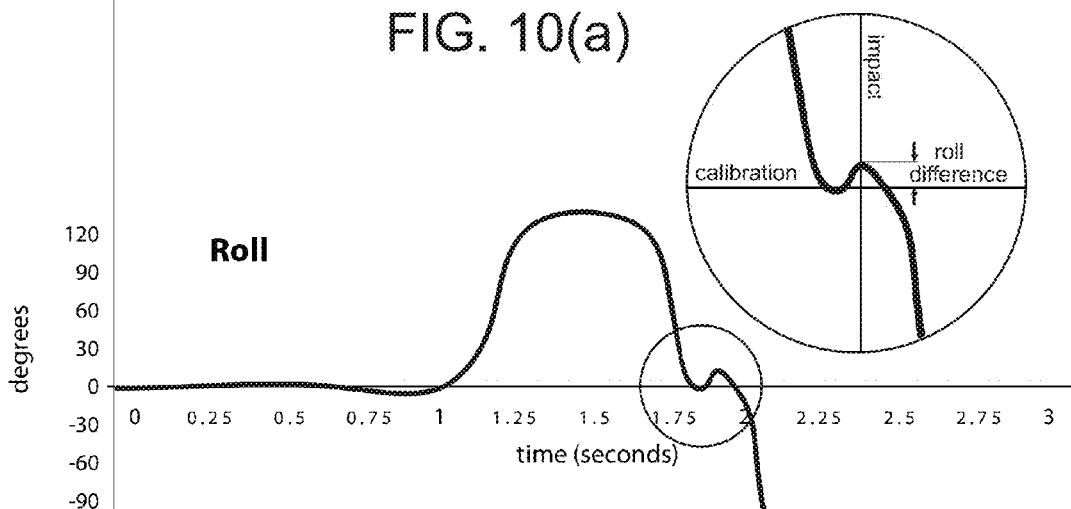
FIG. 10(b)

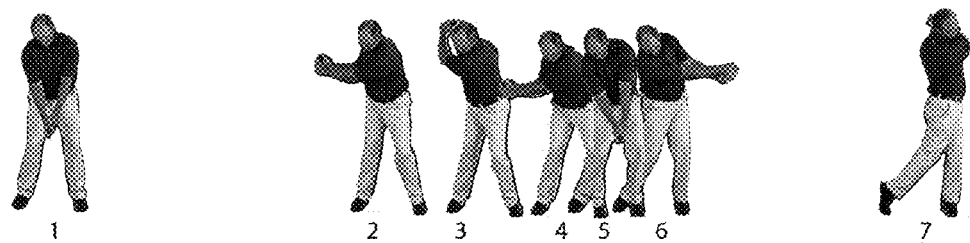
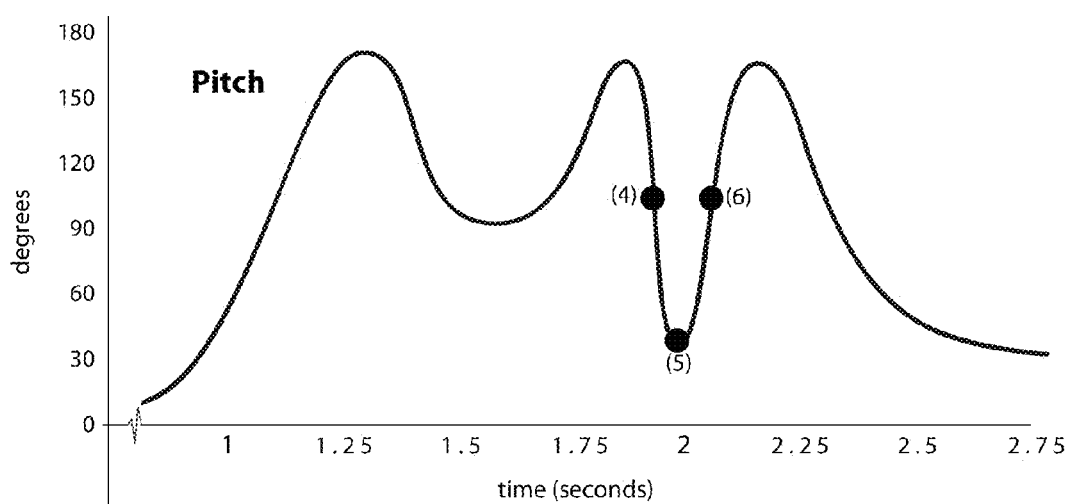
FIG. 11(a)
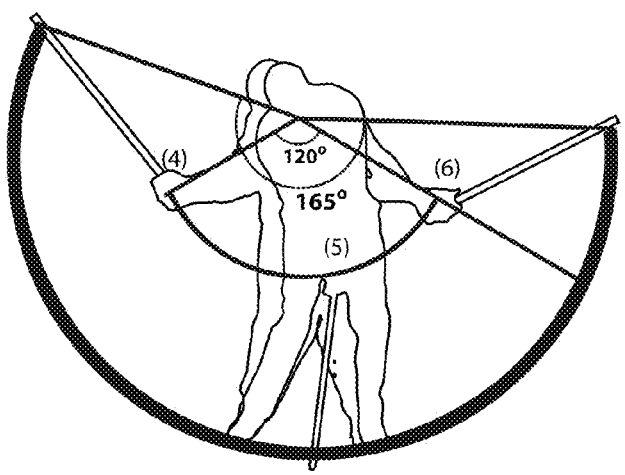
FIG. 11(b)

METHOD TO PROVIDE DYNAMIC CUSTOMIZED SPORTS INSTRUCTION RESPONSIVE TO MOTION OF A MOBILE DEVICE

CROSS-REFERENCE TO RELATED APPLICATIONS

This application is related to and claims the benefit of provisional application Ser. No. 61/551,388 to Jeffery et al., entitled "Using a Mobile Phone With Integrated Motion Sensing For Evaluation of Sports Motions and Providing Customized Sports Instructions Responsive to Said Evaluation", filed on Oct. 25, 2011; and Ser. No. 61/713,813, to Jeffery et al., entitled "Method to Analyze Sports Motions Using Multiple Sensor Information From a Mobile Device", filed on Oct. 15, 2012; each of which is incorporated herein by reference. This application is also related to U.S. patent application Ser. No. 13/269,534, entitled "Method and System For Dynamic Assembly of Multimedia Presentation Threads", by Mark Jeffery, filed Oct. 7, 2011; and U.S. patent application Ser. No. 13/655,366, entitled "Method and System To Analyze Sports Motions Using Motion Sensors of a Mobile Device", filed Oct. 18, 2012, both of which are incorporated herein by reference.

BACKGROUND OF THE INVENTION

1. Field of the Invention

The present invention relates to using a mobile device with integrated motion sensing to evaluate swinging, throwing or other body motions, and dynamically providing customized sports instructions responsive to the evaluation.

2. Description of the Related Art

Conventional sports instruction typically comes in one of three forms. The first is by book or video, written or recorded by a sports professional, explaining proper form, how to correct errors, and how to improve performance, etc. The student has access to a library of content as either chapters in the book or static lessons delivered via the web or on DVD, but he or she then needs to determine which lessons to take, what order to take them and what to focus on. These media may come with a survey that leads the student to lessons they may find valuable, but these lessons often require the student to have some understanding of his or her specific errors.

Golfplan with Paul Azinger is a good example of this approach. The Golfplan iPhone, iPad and Android apps include an initial survey which asks questions and the user then has access to a database of videos which are presented in an order responsive to the survey inputs. These videos are static however, and do not change in sequence unless the user re-takes the initial survey.

The second form of sports instruction is through an in-person lesson with an instructor who determines an athlete's errors by observing the student and/or by using video analysis technology. The instructor then uses their "expert" knowledge to interpret the student's motion errors, demonstrate proper motion, and give the student a practice regimen to perfect his or her form.

The third is highly technical and utilizes more sophisticated analysis of swing data recorded by one of a few technologies. Here a student may attach dedicated hardware motion-sensing devices to their club, racquet, and/or body. Specialized software then analyzes the motion data, typically on a personal computer. An example of such an approach is disclosed in U.S. Published Patent Application No. 2005/0054457 to Eyestone et al. which is assigned to SmartSwing, Inc. Users can also go to motion capture laboratories equipped with computer vision systems that track the motion of a swing and ball flight in two or three dimensions. Technical analysis of swing data can tell a user with great accuracy not only what their errors are but also to what degree they suffer from them. Furthermore, the motion capture analysis data can be utilized for custom fitting of the sports equipment, such as golf clubs and tennis racquets.

Of these three conventional forms, the first including books or video lessons, is the most accessible and lowest cost. The second method of in-person instructor lessons is less convenient and has moderate cost, and the third is often used when an athlete becomes more serious about improving performance and is the highest cost.

SUMMARY OF THE INVENTION

One aspect of the disclosure relates to a method, comprising moving a mobile device having motion sensors integrated therein to simulate a sports motion; evaluating the simulated sports motion to determine at least one topic of interest; selecting, from a content database, content associated with the topic; and displaying the selected content on the mobile device. The motion sensors can include a gyroscope and an accelerometer. In an embodiment, the step of evaluating the simulated sports motions includes evaluating pitch, roll, and yaw of the mobile device. The selected content can include a video clip of an instructor providing swing improvement information, text related to the evaluation of the sports motion, an animation of a proper sports motion, etc. In an embodiment, the method is performed by a processor integral to the mobile device. In an embodiment, the mobile device is held by a user while being moved to simulate the sports motion.

According to another aspect of the disclosure, an apparatus comprises a mobile device having motion sensors integrated therein, the apparatus including a non-transitory computer-readable medium which stores a set of instructions which when executed by a processor of the mobile device performs the steps of the method described above.

According to another aspect of the disclosure, a system comprises a server; a content database linked to the server; and a plurality of mobile devices linked to the server, each of the mobile devices having motion sensors integrated therein; wherein when one of the mobile devices is moved to simulate a sports motion, the sports motion is evaluated to determine at least one topic; a presentation snippet is assembled from content retrieved from the content database; and the presentation snippet is displayed. In an embodiment, the mobile devices are linked to the server via the Internet. In an embodiment, a first one of the mobile devices can be used to simulate a first sport and a second one of the mobile devices is used to simulate a second sport, the first sport and the second sport being different sports. For example, the first one of the mobile devices might be used to evaluate golf swings while the second one of the mobile devices might be used to evaluate baseball swings, the mobile devices connected to the server concurrently. In an embodiment, the presentation snippet is displayed on the same mobile device used to simulate the sports motion. Alternatively, the presentation snippet could be displayed on a display device different from the mobile device used to simulate the sports motion, such as a web-enabled television.

According to another aspect of the disclosure, a method of analyzing sports motions comprises determining a starting point of a sports motion to be simulated using a mobile device having integrated motion sensors; moving the mobile device from the starting point along a path to complete the simulation; obtaining motion data from the motion sensors relating to the starting point and the movement along the path; determining an occurrence of a simulated sports event using the obtained motion data; evaluating the simulated sports motion to determine at least one topic of interest; selecting, from a content database, content associated with the topic; and displaying the selected content on the mobile device or other web enabled display device. In an embodiment, the mobile device is not attached to any piece of sports equipment and the starting point is indicated by the mobile device being held still for a predetermined length of time.

In an embodiment, the sports event is an impact point with a virtual object (e.g., a virtual golf club with a virtual golf ball) The method can further include determining the velocity of the virtual object around the impact point. The velocity can be determined at least in part on velocity of the mobile device around the impact point, arm length, club length, and arc length for the swing type. In an embodiment, velocity is obtained without using data from an accelerometer. Furthermore, determining the velocity can include applying a multiplier based on estimated wrist hinge and forearm rotation as measured by yaw and roll of the mobile device at the impact point. Once velocity is determined, ball flight distance can be determined based at least in part on the determined velocity of the virtual object. In an embodiment, determining the occurrence of the simulated sports event using the obtained motion data includes analyzing the pitch of the mobile device during the simulated sports motion. Determining the occurrence of the simulated sports event can involve analyzing the roll of the mobile device at an impact point, such as by subtracting roll data at the impact point from roll data from the starting point.

In an embodiment, the sports event is an impact point. The impact point can include the impact of a virtual golf club, tennis racquet, baseball bat, ping pong paddle, lacrosse stick, badminton, squash or racquet ball racquet.

In an embodiment, the sports event is a release point. The release point can include a release point of a bowling ball, a lacrosse handle, a basketball, a baseball, a hockey stick, a bean bag, an American football and a fishing rod.

BRIEF DESCRIPTION OF THE DRAWINGS

FIGS. 10(a) and 10(b) illustrate the pitch and roll of the mobile device during an example full golf swing useful for determining swing accuracy;

FIGS. 11(a) and 11(b) illustrate use of pitch data of the mobile device to determine the impact point and the speed of the club head through the impact point;

DETAILED DESCRIPTION OF THE INVENTION

For clarity and consistency, the following definitions are provided for use herein:

As used herein, a mobile device refers to a hand-held device having a microprocessor, memory, and integrated motion sensors.

As used herein, a display device refers to any Internet connected display capable of graphically displaying a web page.

As used herein, a presentation snippet is a component of a multimedia presentation, such a video clip, an animation, a survey, a text message, an audio recording, a hologram and/or any other media content, or a combination thereof.

As used herein, a lesson node is a node of a lesson thread representing at least one presentation snippet.

As used herein, a custom lesson includes the sequence of lesson nodes of a lesson thread, comprising customized multi-media instruction content for a particular user.

As used herein, a calibration point refers to the location in time and space of the mobile device in a set-up position prior to the start of the sports motion.

As used herein, an impact point refers to the location in time and space of impact with a virtual object.

As used herein, a release point refers to the location in time and space of release of a virtual object.

Referring to FIG. 1(a), an exemplary mobile device 160 useable in conjunction with the present invention is illustrated. For illustrative purposes only, the following discussion describes the device 160 in terms of an Apple iPhone available at the time of filing. However, it is to be understood that the discussion is applicable to other mobile phones with motion sensors (e.g., Samsung Galaxy III smart phone), as well as other mobile devices with computing capabilities having motion sensors (e.g., Apple iPod Touch) existing today or later developed. Furthermore, it is to be understood that over time, device capabilities will increase. Indeed, under Moore's Law, the number of transistors that can be placed on an integrated circuit has doubled approximately every two years and this trend is expected to continue for the foreseeable future. Accordingly, it is to be understood that the mobile device 160 described herein is merely meant to provide an example as to how the present invention may be implemented at the current time.

Figure 1:
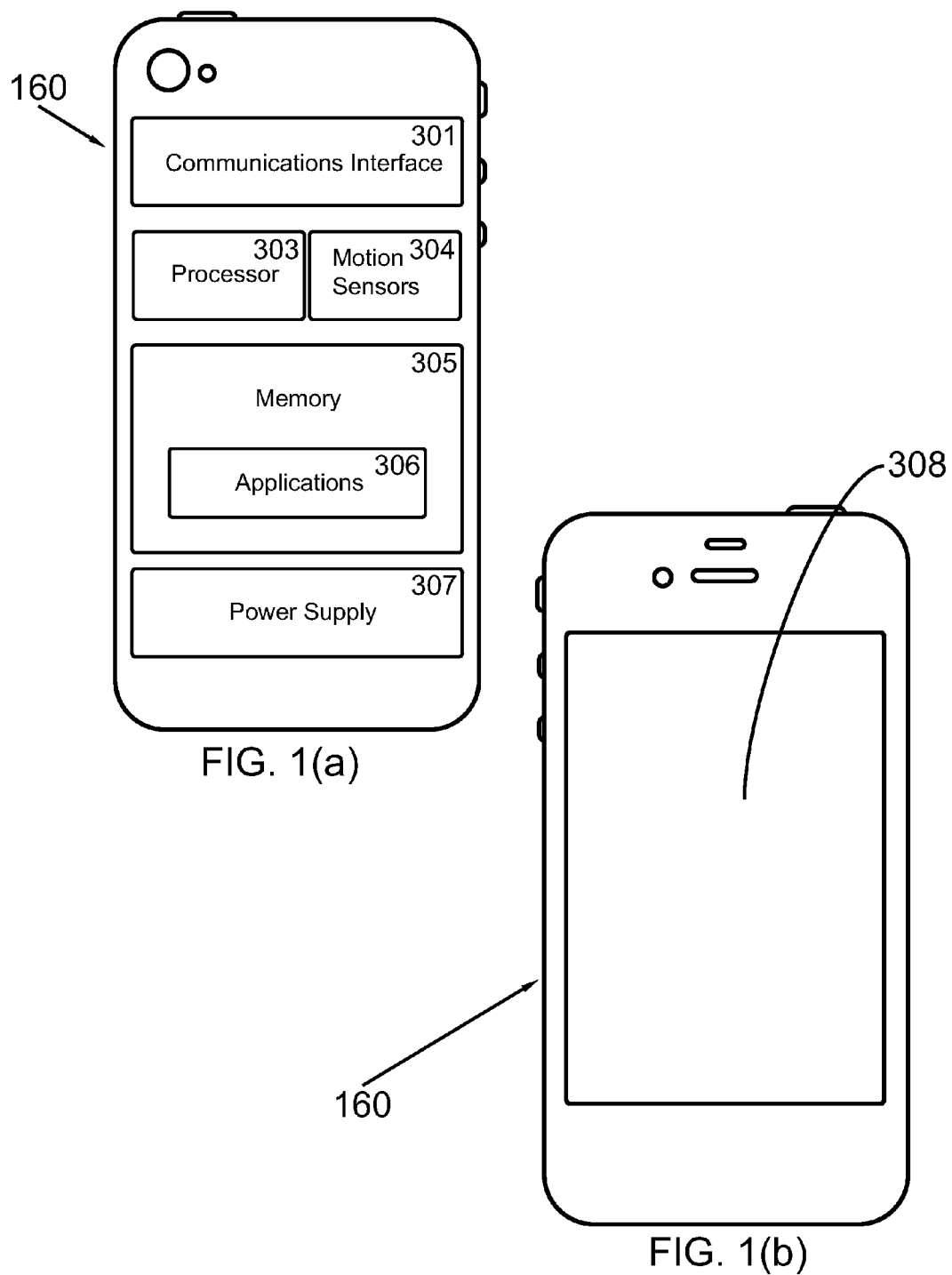
FIG. 1(a) illustrates a block diagram showing the architecture of a mobile device useable in conjunction with the present invention.
FIG. 1(b) illustrates an exterior view of the mobile device.

As shown in FIG. 1 (a), the exemplary mobile device 160 is an Apple iPhone 4S which includes a communication interface 301, a processor 303, motion sensors 304, a memory 305, and a power supply 307. The communication interface 301 controls various input/output devices including a digital camera, a 30-pin dock connector port, a headphone jack, and a built-in speaker and microphone. The communication interface 301 also includes a touchscreen 308, shown in FIG. 1(*b*). The processor 303 is a dual core Apple A5 processor which has a system-on-a-chip (SOC) architecture that integrates the main processor, graphics silicon, and other functions such as a memory controller. The motion sensors 304 can include a three-axis gyroscope to measure a rate of rotation around a particular axis and an accelerometer to measure acceleration in three dimensions X, Y and Z. The memory 305 includes 16 GB, 32 GB, or 64 GB of flash memory (depending on the model). The memory 305 includes storage for an application 306 ("app") which includes the software of the invention. The power supply 307 includes a rechargeable lithium-polymer battery and power charger.

Figure 2:
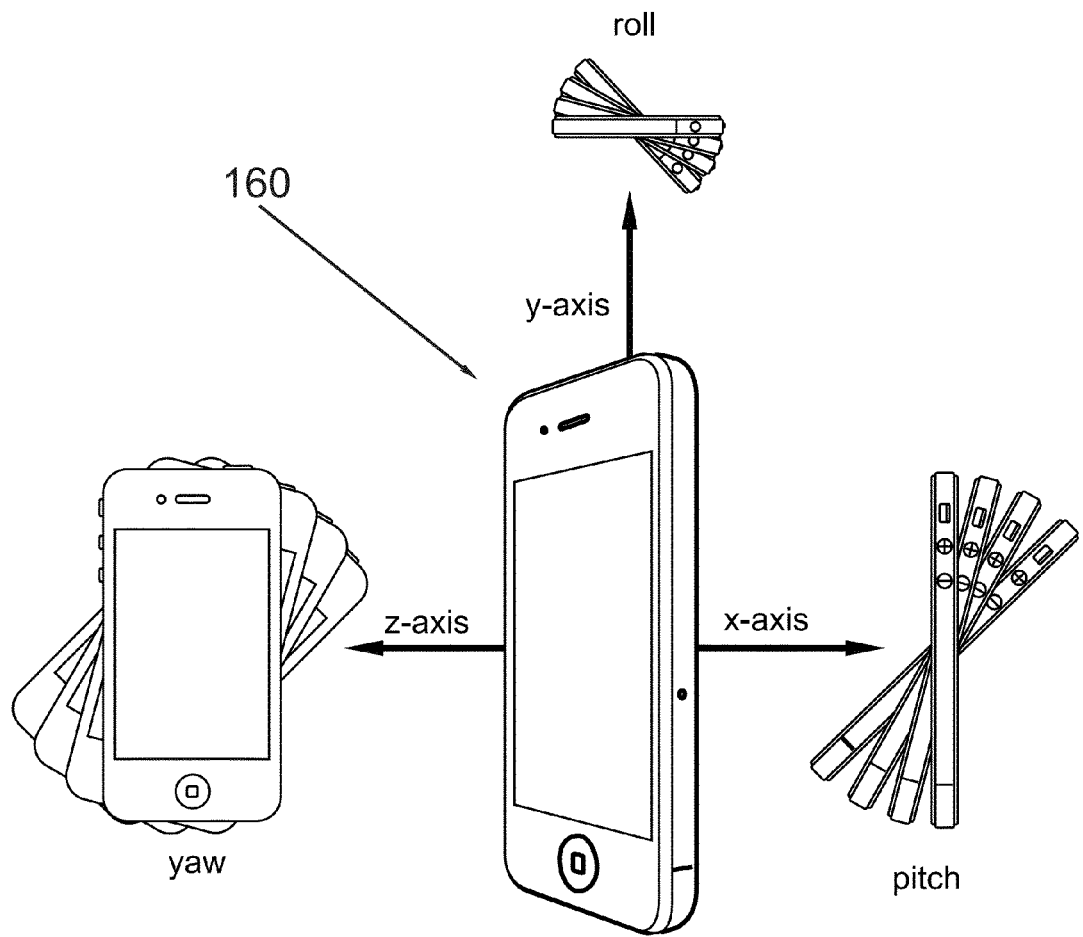
FIG. 2 illustrates types of rotational movement of a mobile device.

FIG. 2 illustrates the various types of rotational movement measured by the motion sensors 304 of the mobile device 160. These sensors 304 include the accelerometer to capture X, Y and Z acceleration data (expressed in G's along a respective axis), and the gyroscope to measure pitch, roll and yaw of the mobile device 160 as it moves (expressed in radians with respect to a respective axis). At present, the motion sensors sample at about 100 times per second (100 hertz), with this data made available (by either polling or having the data pushed) to the application 306 loaded on the mobile device 10. A representative gyroscope useable in conjunction with the present invention is the L3G4200D gyroscope made by STMicroelectronics, Inc. However, it is to be understood that the present invention is not limited to motion sensor technology currently available.

Figure 3:
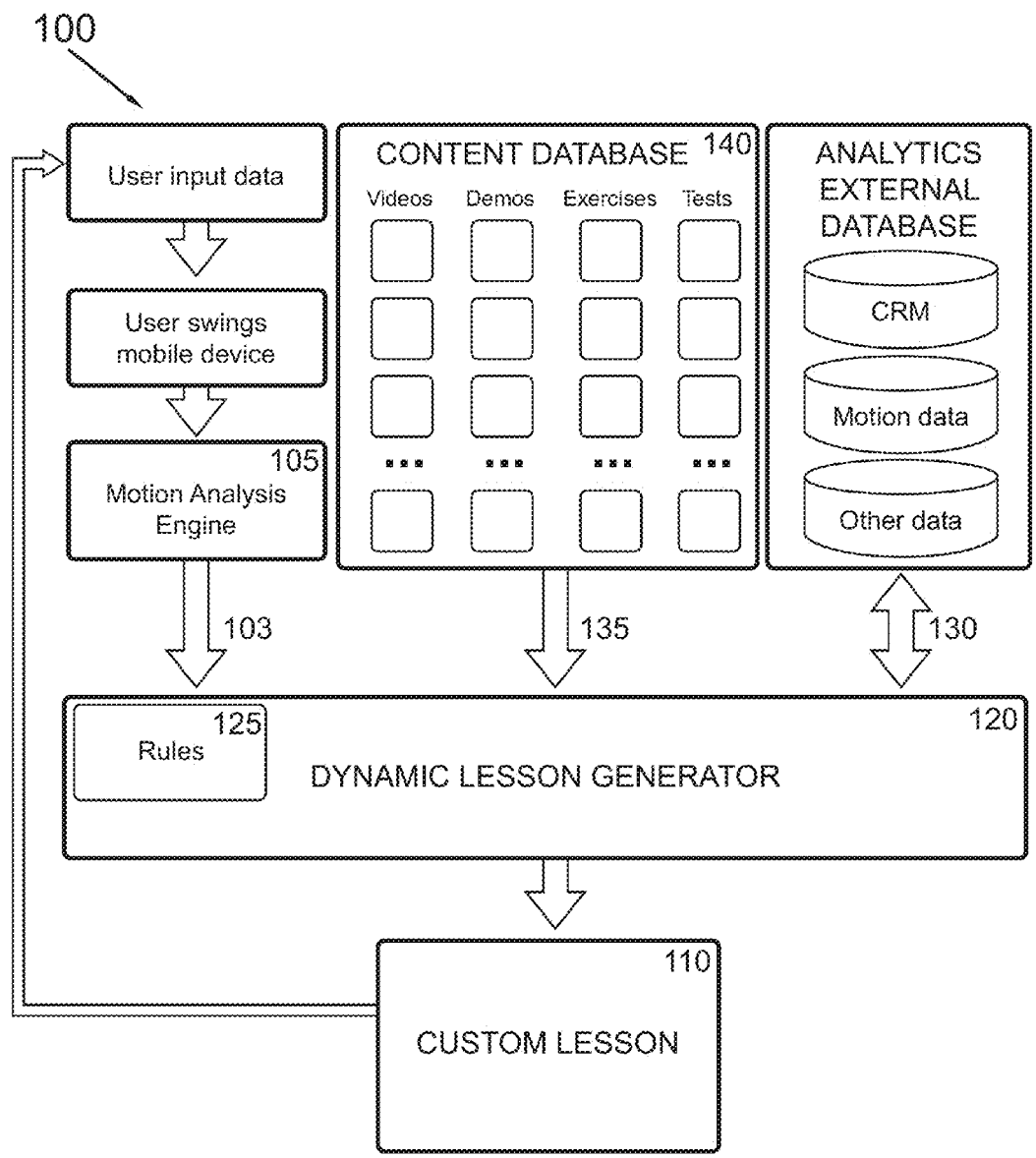
FIG. 3 illustrates an exemplary system for dynamic assembly of custom lessons responsive to motions of a mobile device, according to an embodiment of the present invention.

Referring to FIG. 3, an exemplary system for dynamic assembly of custom lessons 100 is illustrated. The system for dynamic assembly of custom lessons 100 includes a dynamic lesson generator 120 that, responsive to the mobile device swing or other motion analysis inputs 105 and/or analytics/external data 130 (e.g., demographic information, historical swing or other motion data for the user, customer behavior, and preference information), applies a set of rules 125 to generate each of a plurality of presentation lesson nodes, each node consisting of singular or plural snippets, which can be traversed in an order forming a custom lesson 110.

The generated custom lesson 110 can include customized information; thereby creating a multimedia presentation tailored to a particular user responsive to analysis of the user's simulated sports motion captured by the motion sensors 304 of the mobile device 160. The dynamic lesson generator 120 can be a standalone application stored in, and executed using, a single mobile device or implemented on one or more servers accessible by one or more client devices. In an embodiment, the dynamic lesson generator 120 is configured to generate a plurality of custom lessons 110 concurrently, each for one of a plurality of users.

As a user traverses the customized lesson 110, the dynamic lesson generator 120 generates the next lesson node of the customized lesson 110. At each lesson node, at least one presentation snippet, assembled using content 135 from a content database 140, is outputted to the user. The content database 140 can include any organized collection of media files (e.g., text files, audio files, video files). In an embodiment, a plurality of lesson snippet content 135, such as animated simulations and multiple video clips may be assembled into a lesson node, and displayed simultaneously, or in sequence. In an embodiment, the selection, assembly, and ordering depend on the set of rules 125 as well as the capabilities of the user device. In an embodiment, the dynamic lesson generator 120 assembles each presentation snippet from content elements selected from the content database 140 "on the fly" as the user traverses the customized lesson 110. However, in other embodiments, the presentation snippets are pre-assembled, and the pre-assembled presentation snippets are selected from the content database (e.g., as HTML files or video clips). Preferably, the rules 125 are maintained in a separate module, file, or database and can be modified by changing (or replacing) the module, file, or database fields without requiring any change to another component. However, in an embodiment, the rules 125 can be "hard coded" within the application logic.

The techniques of the present invention described herein (e.g., use of the dynamic lesson generator 120 to generate a customized lesson 110) can be accomplished by loading an appropriate application 306 into the memory 305 and executing the application 306. Where the device 160 is the Apple iPhone, the user inputs 105 are received via the user moving the mobile device in a simulated sports motion 306 and interacting with the touch screen 308, and the generated lesson thread 110 can be presented to the user by way of the same touchscreen 306 (and speakers), for example.

An application 306 for the Apple iPhone can be developed using the Apple Developer Suite, including use of Xcode, Interface Builder, and iPhone Simulator development tools, or via custom programming in Objective C. Furthermore, the Apple "Media Player" framework can be used to provide media playback capabilities for the mobile device 160. Apple supports at least the following codecs: H.264 Baseline Profile 3, MPEG-4 Part 2 video in .mov, .m4v, .mpv, or .mp4 containers, as well as AAAC-LC and MP3 formats (for audio). The content database 140 described herein can include a folder (or set of folders) including a collection of media files in supported formats. The media files can exist in the memory 305 or an external server addressable by a URL, for example. For further information regarding programming for the Apple iPhone, see, *Beginning iOS 5 Application Development*, by Wei-Meng Lee (John Wiley & Sons, Inc.), ISBN 978-1-118-14425-1, which is incorporated herein by reference in its entirety. It is to be understood that where the mobile device 160 is other than the Apple iPhone other programming techniques and tools can be used. For example, where the mobile device 160 is a mobile device such as a smartphone or tablet computer utilizing the Android operating system, an appropriate Android software development kit (SDK) can be used to provide the tools and application program interfaces (API) for developing the application 306 on the Android platform using the Java programming language.

Figure 4:
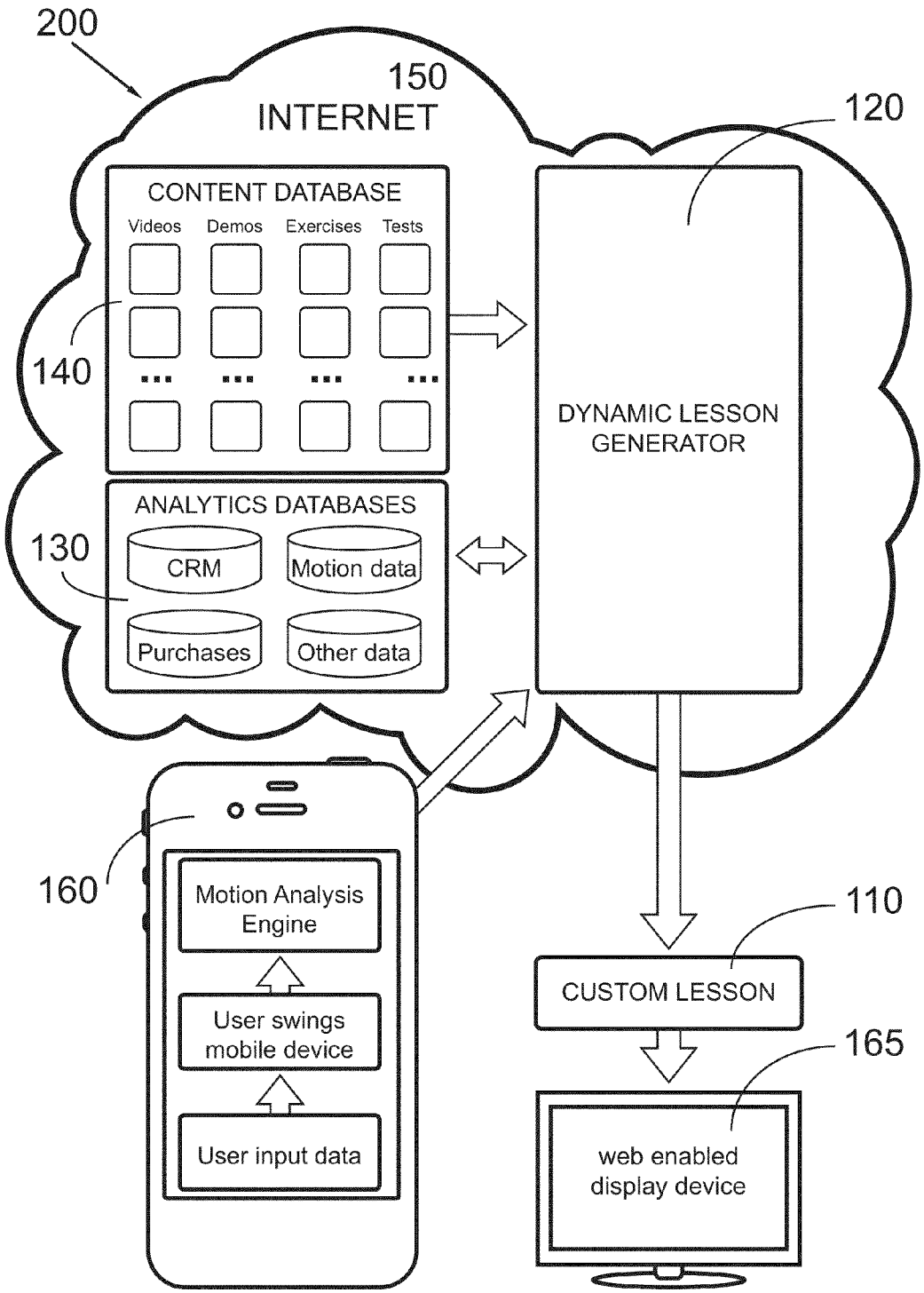
FIG. 4 illustrates an exemplary system for dynamic assembly of custom lessons in a Web-based environment.

FIG. 4 illustrates an exemplary system for dynamic assembly of custom lessons 200, according to another embodiment of the present invention. As shown, the mobile devices 160 and web-enabled display 165 are coupled to the Internet 150. While a single mobile device 160 is shown in FIG. 4, it is to be understood that many more concurrent users and devices may be supported.

Initially, the display device 165 connects to a Web site by the user linking to a URL in a browser. Then, at a presentation layer web server, device information is determined to identify the type of device and browser being used. This may be done in various known ways, such as, for example by obtaining the user-agent string passed by the browser of the device 165 which indicates which browser is being used, its version number, and the operating system and version. The device information is then used to ensure that the presentation snippets created are compliant with the device 165. For example, where the device 165 is a desktop computer with Internet Explorer, the presentation snippets may use Adobe Flash media, but if the device 165 is an Apple iPad with the Safari browser, an alternative format would be chosen. Likewise, the presentation layer web server may determine that a mobile browser will be used. In that case, the web pages outputted to the device 165 may contain information that is easier to view on a smaller screen having a lower resolution. In an embodiment, the presentation snippets include code for display via an HTML5 enabled web browser. HTML5 allows rich multimedia content display on multiple platforms with features designed to make it easy to handle multimedia content without the need to resort to proprietary APIs and plugins.

Additionally, a user-ID can be used to track the user. For an existing user, the user-ID can be provided by the user through an authentication process upon user log-in. New users can be assigned a unique user-ID, such as their email address, and select a password, for example. Furthermore, a thread-ID can be assigned for the particular session for the generated custom lesson 110. Other user information (e.g., demographics, purchase history, preferences, etc.) may also be obtained from various sources, e.g., the analytics/external databases 130, and may be combined with motion data history.

As the user traverses the custom lesson 110, the dynamic lesson generator 120 keeps track of the user's position (current thread node), and generates/selects a presentation snippet associated with the current thread node for display on the user's device 160 and/or the display device 165, where it is presented to the user. User inputs (e.g., output data from swinging the mobile device or touching the screen in response to a question) are sent from the device 160 back to the dynamic lesson generator 120.

It is to be understood that the dynamic lesson generator 120 includes a computer system and software of the invention stored in memory. In the embodiment illustrated in FIG. 4, the computer system can include a central processor, memory (RAM, ROM, etc.), fixed and removable code storage devices (hard drive, floppy drive, CD, DVD, memory stick, etc.), input/output devices (keyboards, display monitors, pointing devices, printers, etc.), and communication devices (Ethernet cards, WiFi cards, modems, etc.). Typical requirements for the computer system include at least one server with at least an INTEL PENTIUM III processor; at least 1 GB RAM; 50 MB available disc space; and a suitable operating system installed, such as LINUX, or WINDOWS 2000, XP, Vista, Windows 7 or 8 by Microsoft Corporation. Representative hardware that may be used in conjunction with the software of the present invention includes the POWER EDGE line of servers by Dell, Inc., the SYSTEM X enterprise servers by IBM, Inc., PROLIANT or INTEGRITY line of servers by Hewlett-Packard, and the SPARC line of servers by Oracle Corporation (formerly Sun Microsystems). The software to accomplish the methods described herein may be stored on a non-transitory, computer-readable medium and may also be transmitted as an information signal, such as for download. The content database 140 can include any computer data storage system, but, preferably, is a relational database organized into logically-related records. Preferably, the content database 140 is an enhanced relational database such as the IBM DB2 Universal Database using IBM's Audio, Image, and Video (AIV) Extenders, to support various media files, or the Oracle InterMedia product which enables an Oracle database to store, manage, and retrieve images, audio, video, in an integrated fashion.

It is to be understood that although not illustrated, the analytics databases 130 can be accessed from external sources each of which have their own computers with central processors, memory (RAM, ROM, etc.), fixed and removable code storage devices (hard drive, floppy drive, CD, DVD, memory stick, etc.), input/output devices (keyboards, display monitors, pointing devices, printers, etc.), and communication devices (Ethernet cards, WiFi cards, modems, etc.). Alternatively, the analytics databases 130 and the content database 140 can be implemented on the same physical computer system.

The analytics databases 130 includes a motion database such that the dynamic lesson generator stores each motion in the system 100. These data can be used for longitudinal tracking of user improvement on various dimensions, and for customizing lesson content responsive to the swing motion history.

Although the Internet 150 is depicted as being used for communication among the illustrated entities, it is to be understood that other network elements could, alternatively, or in addition, be used. These include any combination of wide area networks, local area networks, public switched telephone networks, wireless or wired networks, intranets, or any other distributed processing network or system.

Figure 5:
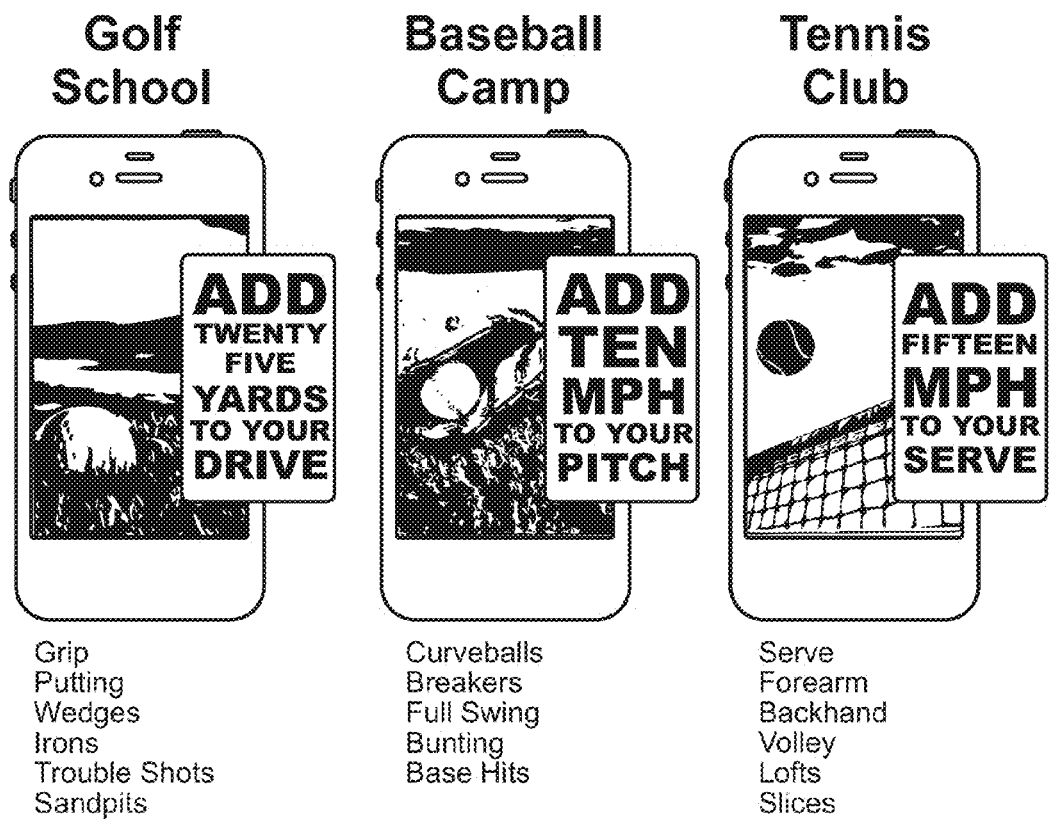
FIG. 5 illustrates several exemplary sports with splash pages initially displayed on a user's mobile device, as well as a list of potential lessons under each.
Figure 6:
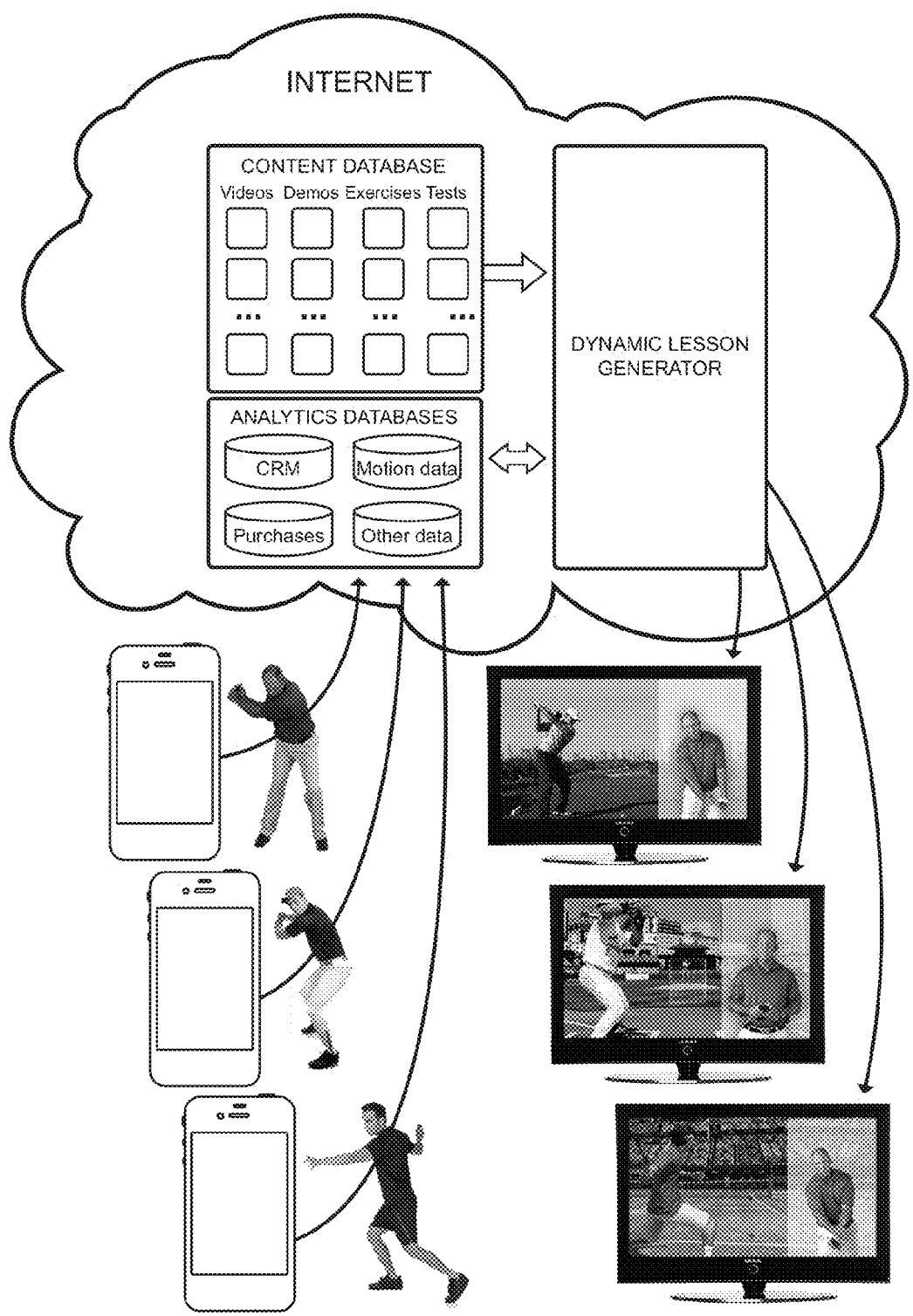
FIG. 6 illustrates an exemplary system for dynamic assembly of custom lessons for different users simultaneously in a Web-based environment, according to another embodiment of the present invention.

Referring to FIGS. 5 to 9, the present invention will be further clarified by examples of sports lessons implemented using techniques described herein, according to an embodiment of the present invention. FIG. 5 illustrates three different splash screens on a mobile device for lessons in golf, baseball, and tennis. FIG. 6 is an embodiment of the web-based method of FIG. 4 for golf, baseball, and tennis sports lessons. In the specific example, FIGS. 7 to 9, the sports lesson is useful for learning how to play golf.

To facilitate understanding, each application is divided into two separate sections. The first is the practice environment where, for example, the user enters a virtual driving range (in the case of golf instruction), batting cage/pitching mound (in the case of baseball instruction), tennis court (in the case of tennis instruction), ski run etc. For impact sports the users hold the mobile device 160 in their hand as a club, bat, ball, or racquet, for release sports the user simulates an actual swing or throw or the user may attach the phone to their leg or arm in a holder as in the case of skiing or boxing respectively, for example. Data gathered by the device's internal gyroscope, accelerometer, and other sensors (such as the compass or Assisted Global Positioning System, AGPS) is then analyzed and relevant feedback (swing speed, orientation, acceleration, estimated ball flight path/distance) is given. Users can enter the practice environment on their mobile devices, and see ball flight following each swing, for example, or can also connect to a web-based version built in HTML, CSS, and Javascript from their personal computer, web-enabled TV or tablet computer.

Using a login/password, users can access an individual practice area. Once inside a personal identification number (PIN) can be shared with friends, or a Uniform Resource Locator (URL) inviting them to download the app and join a shared driving range, batting cage etc. In another embodiment users can see 'friends' who are already logged into the system and can select them from a menu and request they join the individual practice area.

The distributed application is accomplished using a comet (aka Ajax Push, HTTP server push) application that allows the iPhone (or other smartphone or iPod Touch) to push swing data to the browser. As a student practices in the virtual practice facility their swing data is added to a cloud-based database where it is accessible at a later "scoring" section of the app.

Once the user has spent some time in the virtual practice environment and the application has found a baseline for the user's motion the App will alert the user via a "tips pop up" where a professional instructor will appear. The virtual instructor will then tell the user what their most impactful error is and provide a quick tip on how to begin fixing it. If interested, the user can follow the instructor into the second section of each App where he or she can take virtual lessons with a top sports instructor. In the networked embodiment, the 'expert' instruction may appear on the Web enabled device 165, instead of the smart phone 160.

The lesson portion of the system comprises three major components, as previously summarized in FIG. 3: (1) the content database 140, (2) the motion analysis engine 105, and (3) the dynamic lesson generator 120 (including the rules engine 125). The content database 140 can include, but is not limited to, short videos of various instructors discussing elements of various techniques, audio clips, text, 3-D animations and exercises. These elements are the presentation snippets. The motion analysis engine 105 has as inputs the X, Y and Z acceleration from the accelerometer ($a_x$, $a_y$ and $a_z$ respectively) and pitch, yaw and roll of the gyroscope in the smart phone. The motion analysis engine 105 takes the accelerometer and gyroscope data and outputs sport specific variables that are input to the rules engine 125. In coordination with the rules engine 125, the dynamic lesson 120, applying the rules engine creates a customized dynamic lesson (called a presentation thread) for a specific user, which is assembled from the content database to form the presentation snippets. The content is highly customized, and is changed dynamically as the user interacts with the system, following teachings of U.S. patent application Ser. No. 13/269,534. As illustrated in FIG. 6 multiple lessons, in the same or different sports, may be delivered simultaneously and on different web enabled display devices 165, the user positioned so as to be able to view the display for their specific lesson.

Golf School

Figure 7:
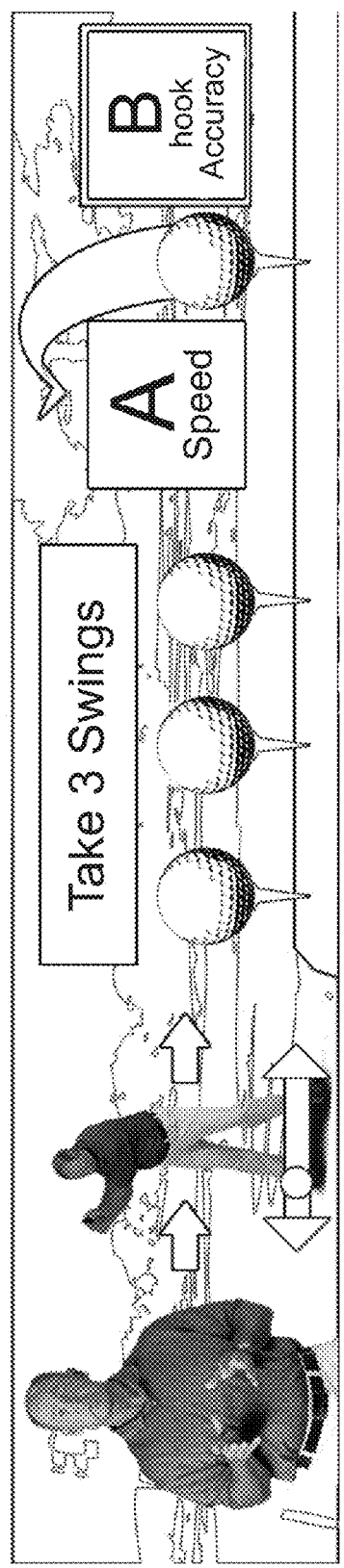
FIG. 7 illustrates an example of a preferred embodiment of a golf lesson, whereby the user takes swings of the mobile device and is graded on their swing speed and accuracy.
Figure 8:
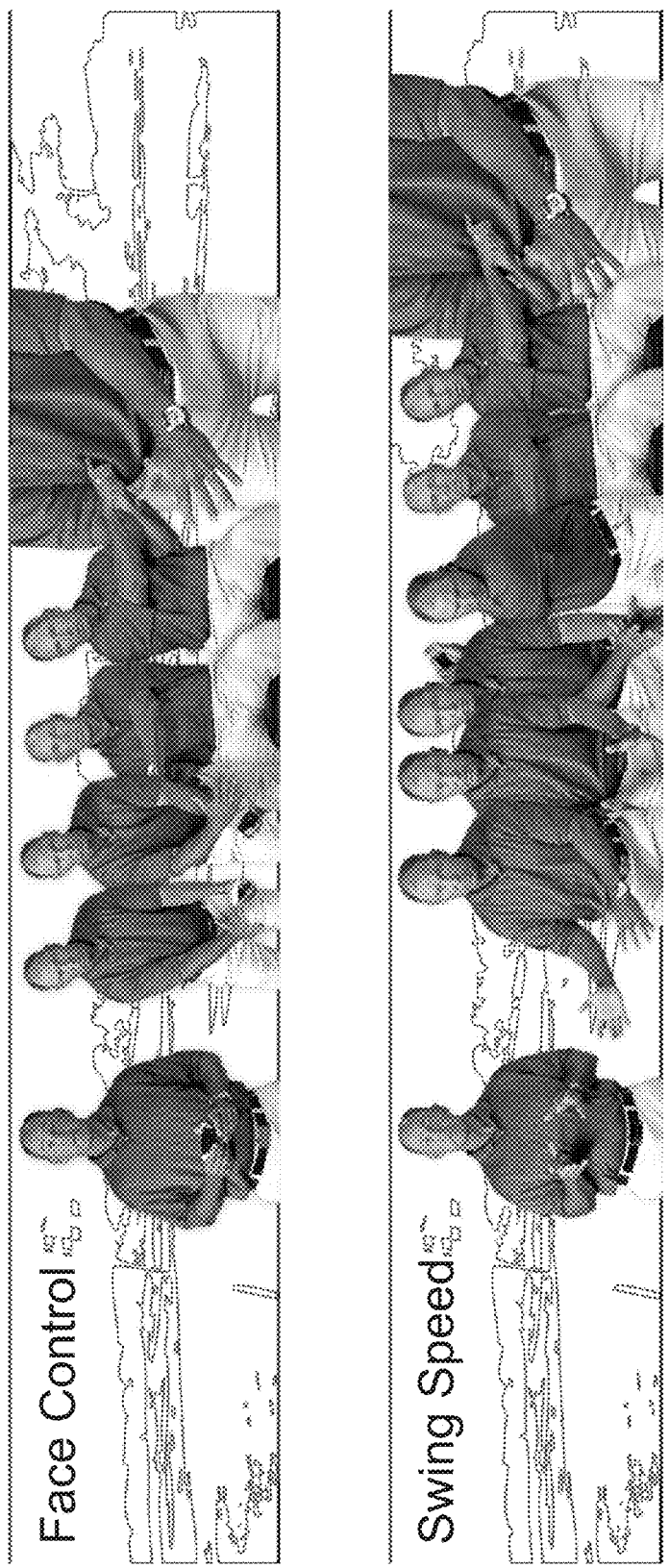
FIG. 8 illustrates customized lessons for face control and swing speed responsive to the motion sensor input.
Figure 9:
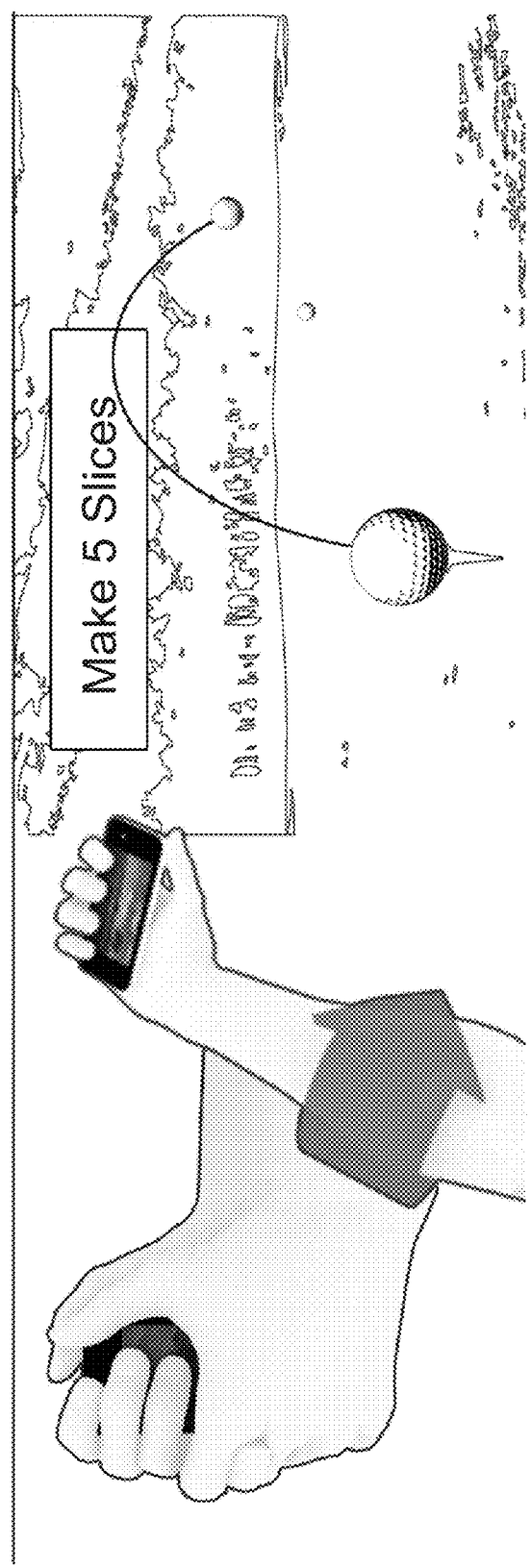
FIG. 9 illustrates a phone-in-hand exercise wherein the user sits in a chair and is asked to take five hooks, five slices and five straight swings.

Referring to FIGS. 7 to 9, the present invention will be further clarified by the following example of a Golf School implemented using techniques described herein, according to an embodiment of the present invention. FIG. 7 illustrates an exemplary sequence of lesson videos, demos, and drills. These figures and the related methods for motion analysis are described in detail herein.

In an embodiment, the Golf School application for the iPhone includes a virtual driving range and a series of lessons on subjects such as the driver, irons, wedges, putting, sand shots etc. The standard driving range is a 'Free' downloadable App where the user can hit only the driver on a basic range. An upgraded driving range is available however, where the user can swipe left or right to choose the specific hole they would like to play and select the specific club they would like to use for the shot. As the user swings the phone held in their hand, their swing is analyzed and the ball flight is animated on the screen of the phone. Additional data is also displayed on the phone screen including, but not limited to, the angle of the phone at impact translated to hook or slice, the calculated speed of the golf club, and the distance a golf ball would travel in yards.

In another preferred embodiment, the user's Golf School phone application is connected to a server where the user has a unique account and identifier. This networked configuration enables the user to swing the phone and see the ball flight and related data on any other web enabled device such as an iPad, PC, or Web-enabled television, see FIG. 4 and FIG. 6. That is, as the user swings the phone the ball flight is animated on a different display, preferably viewable by the user. Furthermore, the user can invite friends to join the practice session on the range, where different players balls are color coded and labeled by the players name or avatar; these friends maybe in the same geographic location or in different geographies simultaneously.

For the golf driver lesson, the value proposition to the user is 'Add twenty five yards to you drive.' This driver lesson includes first, general instruction, including a quick video on the basics of the specific activity followed by an exportable demo that explains the golf swing motion step by step in detail, with graphical overlay of the correct positions of the hands and body at key points in the golf swing. In this demo, the user can zoom in and out, pause, play, reverse, scrub and play at various slow and high speeds. After the user has studied the demo he or she moves to a baseline swing section that asks him or her to take three swings for analysis (see FIG. 7). The user can skip this section and the system will use the data collected from the driving range, or the user can take the three swings. After the three swings are recorded the app gives the user a grade on various dimensions of the swing (generally speed and accuracy) and gives the user a recommendation on which lesson track to start with. This "scoring" section keeps track of every swing the user has ever taken so he or she can refer back to past swings and see their progress.

Once the user has chosen their lesson, he or she will view a series of video snippets and phone-in-hand exercises that focus on the specific errors he or she suffers from—for the golf driver lesson accuracy track this could be a slice or hook, in speed it could be casting, lag, improper forearm rotation, or wrist hinge, see FIG. 8. In tennis, an accuracy error is over rotation as the forearm swings or high-low swing path, in speed it could be improper coiling and uncoiling. In baseball an accuracy error could be a swing bubble at impact due to improper forearm rotation. Whatever the sport, output of the motion analyzer is used by the rules engine to define the error(s) of the user, and the lesson is customized to fix the error(s).

During the lesson the instructor will prescribe a drill or drills to correct the specific error. The drills are varied depending on which types of feedback work best with each activity, but are designed so that the user can return to them for any amount of time convenient to their schedules. In the golf accuracy lesson for example, see FIG. 9, a drill is to sit in a chair and hold the phone out straight from the body. They then swing the phone back and forth while rotating their forearms. This forearm rotation is intimately related to hooking or slicing the golf ball, and audio feedback is given in terms of a sound driven from the gyroscope or the expert instructor saying "good", "good", "hook", "slice", etc, for example. That is, immediate feedback is given responsive to the motion sensor input.

As another example, for the speed drill the user sits down in a chair, holds the phone out in front of himself, waits for a calibration vibration, then rotates back and then through the swing. The drill is designed to teach the user to control and accelerate their speed while maintaining a square club face. The user starts slow and each time he or she drives, through audio feedback, the instructor will tell the user whether he or she swung faster or slower than the previous swing, and how the accuracy compared to the last swing. The challenge is to slowly build speed while maintaining excellent rotation timing with a square phone (club head) at impact. If the user swings and over or under rotates, the instructor provides audio feedback that he must slow back down and try again. After the user finishes a lesson thread he or she can return to the baseline swing section to see if they can improve their scores.

Specifically, in the Golf School "Add 25 Yards To Your Drive", lesson Mike Malaska, 2011 PGA Golf Teaching Professional, teaches via video snippets how to correct yard stealing errors in full swing drives. The thread starts with an introduction that discusses where a golfer should focus their attention, arm movements. Then Mr. Malaska goes into a driver demo where he discusses all of the stages of the swing and proper arm, forearm, and wrist positions at each stage. The user then moves to their baseline swings and scoring. Once scored by the motion analyzer, the user can go to a speed or accuracy lesson. The speed lesson is a series of two minute videos on how specifically the arms, the forearms, and the wrists each build speed individually.

The control lesson is a series of two minute videos that explain timing, and based on your swing score's error, how to correct a slice or hook with. The drill has the user sit in a chair and swing through, receiving feedback after each swing on how square he or she were at impact. Once the user understands the motion, Mr. Malaska has the user swing five hooks, then five slices, then five straight. This builds an understanding and connection between hand positions and ball flight. Once the user can consistently produce the different types of swings, Mr. Malaska has the user swing through a range, starting with a large hook (or a swing with a very closed face at impact) then moving slowly to a less closed face (draw), then a square clubface (straight), then a slightly open clubface (fade), and finally a very open club face (slice). Once the user can control, finely the face of the club at impact, he or she will be able to control where the ball goes on the fairway.

Note that these content are customized based upon the swing motion analysis and the area the user choose to focus on. For example, if the user selects accuracy as an area to focus on then the key motion analyzer variable is the roll of the phone, which is translated into degrees of hook or slice. The system then customizes the lesson so that a user who hooks will see different content to that of a user who slices. Furthermore, in a preferred embodiment additional user input can customize the thread content. For example, there is an option for the user to enter height, average driving distance, gender, and left or right handedness. So that a female golfer, who is left handed and hits the driver 200 yards may see a top female golf instructor, with videos mirrored for left handedness, and driver distances scale to an average of 200 yards.

Furthermore, the golf lessons may utilize the web-enabled display device 165 of FIGS. 4 and 6. So that for example, with the web-enabled display device 165 positioned so that the user can see the web-enabled display device 165, the instructor (Malaska) can show two virtual sticks (like a goal post) on the web display. Where the exercise is for users to hit virtual balls, via swinging their mobile device, left, right and straight through the sticks. In order to master this exercise, students must understand how to systematically hook, slice and hit straight shots. After two or three swings, customized lesson snippets are presented on the web enabled display responsive to the swing analysis of the student. This simulation is a virtual experience closest to having an actual instructor standing next to the student.

The Golf School contains many lessons that the user can select, downloadable for a fee. These lessons include but are not limited to: driver, irons, wedges, putting, fairway bunker shots, short game chipping, sand shots, play for the first time, and golf fitness. Furthermore, lessons are customized to different levels of proficiency so that the expert player sees different content and exercises than a beginner.

A preferred embodiment also includes a "playing lesson". A 'playing lesson' enables the user to swing the phone while on the actual golf course. Customized instruction is then provided as a quick fix for errors detected by the phone in the swing. For example, perhaps the user starts to slice the golf ball while playing the game. The phone will detect the error and the expert instructor will suggest a quick fix of closing the club head (phone face) at address. The user may also take a few practice swings with their mobile device prior to each shot, and receive expert instructor feedback.

A notable aspect of our invention is the motion analyzer which uses the accelerometer and gyroscope embedded within the mobile device 160. FIG. 10 illustrates the pitch and roll of the mobile device 160 during an example full golf swing. An important element of the present invention is the calibration of the mobile device 160 by holding the mobile device 160 still in the address position (position 1), see FIG. 10(*a*). The motion signature for the pitch then increases in the backswing (position 2) and has a local minimum at the top of the golf backswing (position 3). However, the minimum (position 3) is an artifact of the pitch motion sensor rotating more than 180 degrees. In actuality, the pitch continues to increase to a maximum, greater than 180 degrees, at the top of the backswing. However, limitations of the sensor constrain the motion signature to 0 to 180 degrees. The pitch data continues to decrease in the downswing (position 4), back to the impact point (position 5), as shown.

Accuracy Analysis

Note that at the impact point, position 5 in FIG. 10(*a*), the mobile device 160 has returned to near the initial calibration point (position 1), which for golf is the hand position at impact with a virtual golf ball and a local minimum. For a high speed golf swing the minimum at the impact point does not return exactly to the calibration zero due to resolution limits of the gyroscope. Determining the impact point is of vital importance because the roll of the mobile device 160 at this point defines the hook or slice of the club. In other sports, the impact point is vital in determining the hook and slice of a bat or a racquet, and/or the release point in throwing or casting sports. From the impact point, the golf swing continues through follow through, positions (6) and (7).

In summary, pitch data FIG. 10 (*a*), or the rotation around the axis that cuts the mobile device 160 into top and bottom halves when looking at the screen (X-axis) (see FIG. 2) is the most telling data stream as a golfer moves through their swing. Impact can be found at the major minimum that approaches the starting calibration point (which is defined as "zero" by taking the average of all phone position/orientation data over the course of one second (for example) taken prior to the swing when the golfer is in their set-up position). To bring context, in a golfer's swing, pitch data rises as the golfer goes into their backswing, returns to calibration as he or she swing through impact, then rises again as he or she moves into their follow through. Impact is the pitch position that gets closest to the set-up, or calibration point.

Once impact is found, swing accuracy is determined by subtracting roll data at impact from roll data at calibration, see FIG. 10 (*b*). Roll data, or the rotation around the axis that cuts the phone into left and right halves when looking at the screen (Y-axis) describes "open and closed" face positions on the club head. FIG. 10 (*b*) shows an expanded view of the roll data. Swings that return a negative difference mean that the user over-rotated at impact which implies a closed face at impact and a resulting draw or hook depending on the amount. Swings that return a positive difference mean that the user under-rotated at impact which implies an open face at impact and a resulting fade or slice. Swings that return a near zero value mean the club face very closely matched calibration orientation at impact and imply a straight ball flight.

Speed Analysis

Club head speed is a critical parameter for golf in defining the ball flight distance. Golf club manufacturers have empirical tables which detail the ball flight distance for golf balls hit by club heads moving at a specific swing speeds. Such tables also take into consideration the club type (e.g., driver, 5-iron, putter), the club head loft, the shaft stiffness, and other variables that impact the ball flight.

Swing speed is a complex calculation due to the mechanics of sports motions. The challenge is that the mobile device sensors 304 measure motions of the hands whereas we are interested in calculating the speed of virtual sports equipment, such as a golf club head. Extensive experiments with professional athletes were conducted using appropriately fitted sports equipment to understand how hand and arm motions translate to the motion sensor data outputs. While the analysis for golf is illustrated, it is to be appreciated that the present method is generalizable to other sports motions, such as, but not limited to, those found in the sports of baseball, tennis, bowling, basketball, American football and table tennis.

If the club is swung exactly in line with the arms, then the mobile device velocity, V, is related to the club head velocity (V club head) by:

$$V_{club\ head} = V \times (\text{Arm Length} + \text{Club Length})/\text{Arm Length} \quad (1)$$

However, expert golf players hinge their wrist and rotate their forearms to increase the velocity of the club head through the ball. These hinging and rotating motions can dramatically increase the velocity of the club head through impact, so that Equation (1) is a gross under estimate of the golf swing speed for most golfers. It is a good for putting, however, since there is no hinging of the wrists.

FIG. 11 illustrates specifically how we calculate the speed of the mobile device 160 for a golf swing. The motion signature for the pitch of the mobile device 160 for an example full golf swing is graphically illustrated. Shown below is the corresponding sports motion with points (4), (5) and (6) in pitch data labeled on the swing. We first find the impact point in pitch data, defined as the local minimum of pitch at the bottom of the swing (point 5). We then look forward and back in pitch data by 60 degrees. These data points, assuming proper wrist hinging, align with positions in the swing (4) and (6). Generally, about one tenth of a second passes between these two positions, so that given the player's arm length we can find the mobile device speed 160 around impact by dividing the length of a 120 degree arc where the radius of the arc is equal to the arm length by the amount of time passed: This delivers the speed of the mobile device 160 (hand speed). A similar method can be used for chipping but with a shorter arc length of 55 degrees or less due to the reduced swing length.

It has been found, using high speed video clocking, that the driver club head speed can be as slow as 2.4 times hand speed (this is in the case of a user swinging a club with rigid arms, forearms, and wrists) or as fast as 6 times hand speed (in the case of a world class professional golfer). The difference between these two multipliers comes from the combination of forearm rotation and wrist hinge which allow golfers to force the club head to travel through a much greater arc length (sometimes even close to 180 degrees) in the time it takes the hands to travel through the 90 degrees of arc length around impact. The multiplier we choose is driven directly by gyroscope acceleration through impact on the Z and Y axis (yaw and roll) which account for wrist hinge and forearm rotation respectively.

From detailed experiments with the iPhone 4 and 4s it was found that the gyroscope is particularly accurate, so that the roll data is very good to predict hook or slice within approximately half a degree. The accelerometer data from the iPhone 4, however, is "noisy", and is not particularly accurate over the entire golf swing, but does work well for measuring forearm rotation rate around impact. This is why we divide the swing into portions and calculate an average velocity, V, of the mobile device through impact:

$$V = \frac{D_2^{10} - D_1}{t_2 - t_1} \quad (2)$$

where $D_2-D_1$ is the distance between points (4) and (6) in FIG. 11; and $t_2-t_1$ is the time taken to cover the distance $D_2-D_1$. A shorter distance is preferred, since this enables a closer approximation of the instantaneous velocity at the impact point. However the 0.01 sec resolution of the current gyroscope requires us to use the 120 degree arc. In the future, as the sampling resolution of the gyroscope increases, a 30 degree arc or less will be preferred.

Equation (2) is an approximation of the actual instantaneous velocity of the phone, and is only a first order approximation of the speed of the golf club head, since it does not include the wrist hinge or forearm rotation described above. Via detailed experiments with a high-speed video camera we were able to find multipliers for these variables, with the result of calculating club head speed within +/−10% for a variety of swing types. From club head speed we can predict ball flight distance in ideal conditions.

We envision that the data quality output from the accelerometer will improve dramatically in future versions of iPhone or Android based phones. In an embodiment of the present invention, the velocity of a mobile device 10 (having a sufficiently accurate accelerometer) at impact is calculated by integrating the acceleration from the top of the backswing ($t_{bs}$) to the zero ($t_0$) of the mobile device:

$$V_x = \int_{t_{bs}}^{t_0} a_x dx$$

$$V_y = \int_{t_{bs}}^{t_0} a_y dy$$

$$V_z = \int_{t_{bs}}^{t_0} a_z dz \quad (3)$$

with the total mobile device velocity at impact:

$$V = \sqrt{V_x^2 + V_y^2 + V_z^2} \quad (4)$$

where $t_0-t_{bs}$ is the time between the minimal at the top of the back swing ($t_{bs}$) measured from the pitch data and the zero at the bottom of the swing at impact, $t_0$. The integrals are calculating in the software using a fourth order Runge-Kutta algorithm. See for example, William H. Press et al, Numerical Recipes 3rd Edition: The Art of Scientific Computing, 2007.

The velocity component vectors (4) are difficult to accurately calculate with the current version of the accelerometers, since the internal accelerometer has a noisy output, hence why we currently use the average method equation (2). Data on the swing motion is presented to the user and stored, local to the app and on a server in the user's account, for longitudinal comparisons of swing consistency improvement.

Baseball Example

Figures 12A, 12B, 12C:
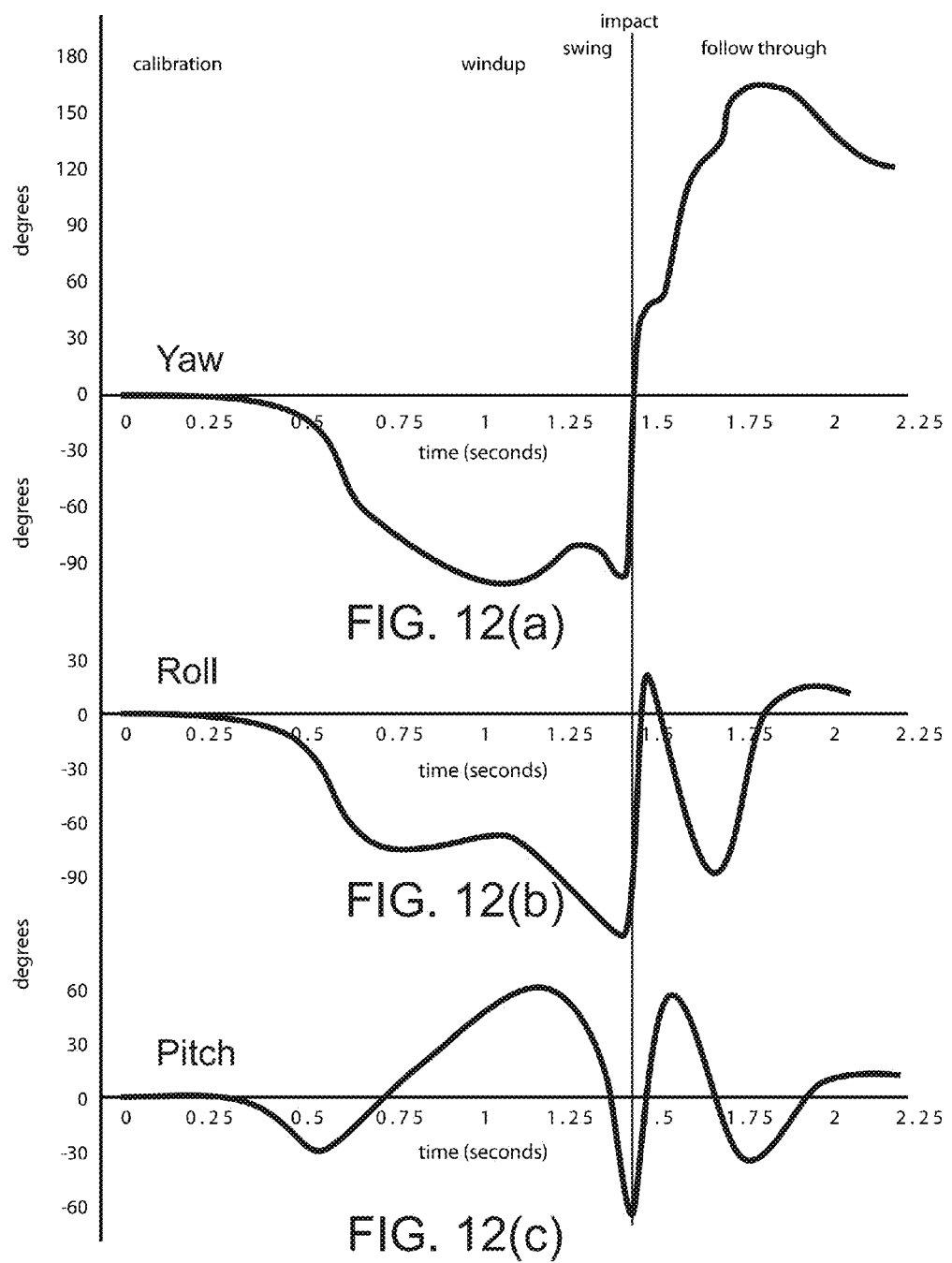
FIGS. 12(a) to 12(c) illustrate yaw, roll and pitch for a baseball swing.

To illustrate the preferred embodiments where the sports motion is other than golf, we provide an example for baseball. Analysis of other sports such as, but not limited to, tennis, bowling, basketball, American football or fly fishing follow similarly. Baseball swing motion sensor data is illustrated in FIG. 12. For a baseball swing the calibration point is a set-up position with the mobile device 160 held in both hands out in front of the body, with the thumbs pointing so as to naturally line up the mobile device (virtual bat) with a ball on a virtual tee; the hands are perpendicular to the ground. The data shown in FIG. 12 is from a professional athlete and illustrates the essential features of an optimal baseball swing motion. For the baseball sports motion, yaw is the key variable, see FIG. 12 (*a*), since as the "bat" is swung through the impact point with a virtual ball, the ideal hand position is with the palms parallel to the ground, which causes a rapid change in yaw of the mobile device through impact. The yaw at the calibration point was zero; hence the impact point is when the yaw crosses zero, see FIG. 12 (*a*), even though the mobile device is rotated ninety degrees relative to the calibration point. In an ideal baseball swing the roll of the bat occurs just after the impact point, see FIG. 12 (*b*). In the event there is a roll maximum at the impact point, then the wrists have a tendency to lift the bat over the top of the ball, causing a ground or missed ball: this is the "swing bubble."

The pitch and yaw of the mobile device 160 taken together provide insights into the angle of the bat through the impact point. For example, the pitch data in FIG. 12 (*c*) shows that the hands sloped downward at the impact point, since the pitch is negative at the impact point and does not return to zero until after the impact point, and hence the bat would have contacted the virtual ball if it were thrown below the calibration point, that is, in the lower half of the strike zone. Hence, the baseball swing motion data FIG. 12 can be input into the systems FIG. 3 or FIG. 4 and dynamic lessons generated responsive to the motion input.

Bowling Example

The examples thus far have focused on sports such that the sports motion impacts virtual objects such that the impact point and release point are in the same location in time and space: i.e hitting a golf or baseball with a golf club or baseball bat respectively. The method is not limited to these examples however, and can be applied to other sports where the release point is different from the impact point, or where there is no impact point and only a release point, or when the release point is different from the calibration point. Examples include a bowling ball throw, a baseball pitch, a basketball free throw, a bean bag toss, an American football throw, or casting of a fly fishing hook. It is to be understood that these examples are for illustration and are not limiting.

Figures 13A, 13B, 13C:
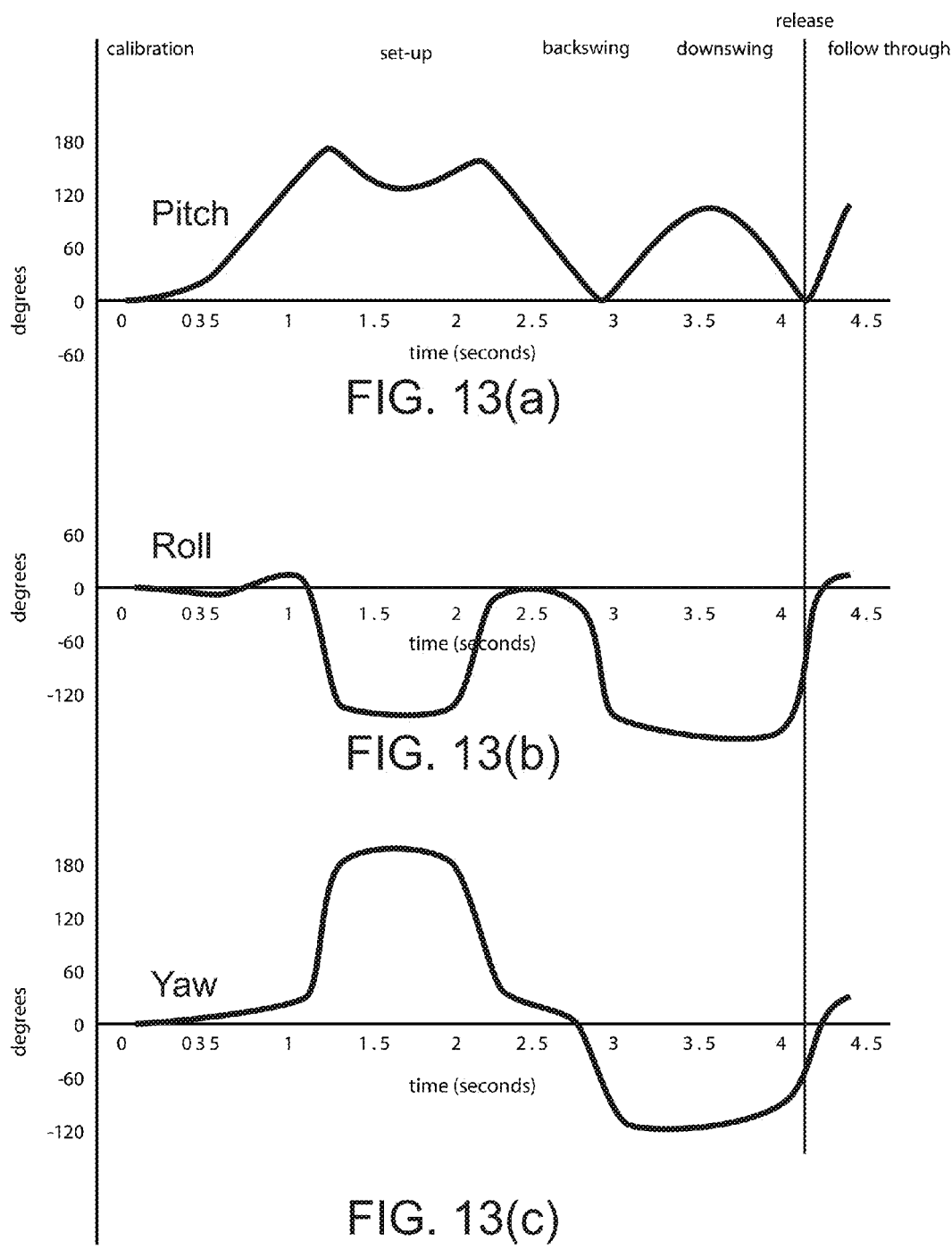
FIGS. 13(a) to 13(c) illustrate pitch and roll for a bowling motion.
Figure 14A:
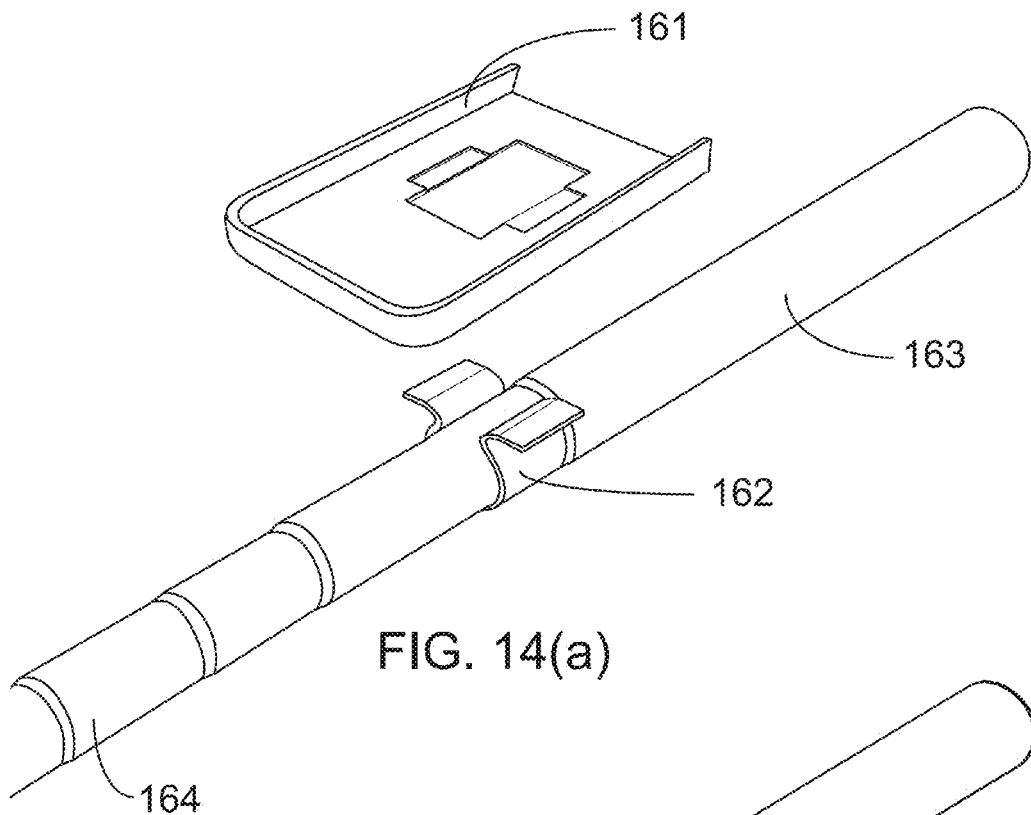
FIGS. 14(a) and 14(b) illustrate an example mobile device holder mounted to an ancillary device.
Figure 14B:
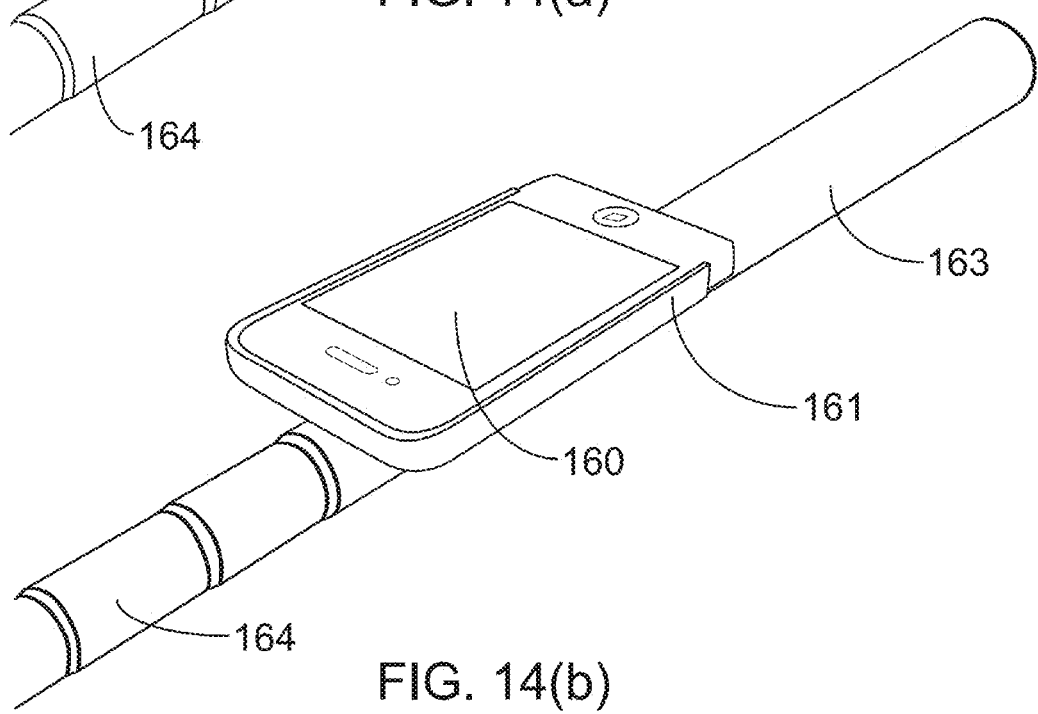

In all cases the motion signature is analyzed similar to the prior examples. As a specific example, FIG. 13 illustrates the mobile device motion sensor data for a bowling sports motion. In this example, the calibration point is the hand at rest, relaxed and fully extended at the player's side, with the palm of the hand facing forward. The bowling motion is to first bring the virtual bowling ball up to the chin, cradled in both hands, and then to swing down and forwards while taking a few steps. The pitch data illustrates how the pitch of the mobile device 160 increases as the mobile device 160 is brought up to the chin, where there is a local minimum as the player starts to step forward. Then, the pitch decreases as the player swings down in the backswing motion, where there is a zero of pitch corresponding to the initial calibration zero, and then the motion transitions to the final downswings to a second zero, which is the release point of the virtual bowling ball.

Similar to the golf swing described previously, the velocity of the virtual bowling ball can be calculated from Eq. (2) and the time difference between 30 or 60 degree pitch points, similar to FIG. 11, or via integrating Eq.'s (3). The rate of change of the roll data, the derivative of roll, through the release point is proportional to the spin rate imparted to the virtual bowling ball. Hence we can calculate the velocity and spin of the virtual bowling ball at the release point.

Note in this example the release point is different in space from the calibration point, and the impact point is further removed from the release point. In this example, the impact point occurs in virtual space. Using a cloud-based system described previously for golf, see FIG. 4, the bowling ball can be displayed on a virtual bowling lane on an HTML5 web-enabled display, such as a web TV, and the impact with the pins simulated in time and space given the velocity and spin of the virtual bowling ball, and the length of the virtual bowling lane. Hence, the player executes the virtual bowling motion, and sees the virtual bowling ball go down the lane and hit the pins on the Web-enabled display, with a path and speed determined by the velocity and spin calculated from the swing signature of the mobile device and synchronized in time to appear like a continuous motion. Lesson nodes, with singular or multiple presentation snippets, can then be displayed on the web-enabled display or the mobile device responsive to the bowling swing analysis.

Attachment to an Ancillary Device

Thus far, the description of the invention has been limited to use of the mobile device 160 to simulate a sports motion by the user holding the mobile device 160 in his or her hand and moving the mobile device 160 in a certain manner (e.g., swinging the mobile device 160 as if it were a golf club). However, advanced players may find it desirable to feel the grip of the sports equipment in sports such as golf, baseball, tennis or fly fishing, for example. In the case of golf, for a right handed player, advanced players may have a grip on the club so that the left hand is rotated approximately 20 degrees from center towards the body. Such a grip on the golf club handle enables the club head to be more closed through impact which in turn makes it easier to draw the golf ball, that is, create a ball flight that bends to the left.

The methods of the present invention relating to analysis of sports motions are generalizable to also include attachment of the mobile device to sports equipment, or to weighted grips simulating the sports equipment.

As an example, FIG. 13 shows a mobile device holder 161 to securely mount the mobile device 160 to an ancillary device 163 via an interlocking clip 162, which in the illustrated embodiment is a physical golf club but could instead (for golf) be a weighted golf grip. In an embodiment, the ancillary device 163 is comprised of a 24" long steel or graphite golf club shaft with a golf grip at one end and a 6 ounce weight at the other. Preferably, the entire ancillary device 163 weighs approximately 11 ounces (similar to a golf club driver), and the center of mass is approximately 6-8" inches from the weight, so as to simulate an actual golf club, which typically has the center of mass approximately ¼-⅓ the length of the shaft closer to the club head. FIG. 12 is presented for illustrative purposes, and is not meant to be limiting. Other sports, such as baseball, tennis, and fly fishing, would have different ancillary devices but the grip, weighting and center of mass more accurately simulate the actual sports equipment, and/or the mobile device could be attached to the actual sports equipment via the holder 161.

While this invention has been described in conjunction with the various exemplary embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

What is claimed is:

1. A method, comprising:
holding a mobile device directly in at least one hand, the mobile device having motion sensors integrated therein;
moving the hand-held mobile device to simulate a sports motion;

evaluating the simulated sports motion to determine at least one topic of interest,
wherein evaluation of the sports motion includes analyzing a first gyroscope sensor data and a second gyroscope sensor data to determine an impact point or release point;
selecting, from a content database, content associated with the topic; and
displaying the selected content on the mobile device.

2. The method of claim 1, wherein the motion sensors include a gyroscope and an accelerometer.

3. The method of claim 1, wherein the step of evaluating the simulated sports motions includes evaluating pitch, roll, and yaw of the mobile device.

4. The method of claim 1, wherein the mobile device includes a phone.

5. The method of claim 1, wherein the selected content includes a video clip of an instructor providing motion improvement information.

6. The method of claim 1, wherein the method is performed by a processor integral to the mobile device.

7. The method of claim 1, wherein the mobile device is held by a user while being moved.

8. The method of claim 1, further comprising storing motion data related to motions of the mobile device during the simulated sports motion in a database.

9. The method of claim 1, wherein selecting the content includes obtaining content based on one or more of user input data, prior motion data, and CRM data, and assembling the obtained content, the selecting and assembling according to a set of predetermined rules.

10. An apparatus comprising a mobile device having motion sensors integrated therein, the apparatus including a non-transitory computer-readable medium which stores a set of instructions which when executed by a processor of the mobile device performs the steps of:
holding a mobile device directly in at least one hand, the mobile device having motion sensors integrated therein;
moving the hand-held mobile device to simulate a sports motion;
evaluating the simulated sports motion to determine at least one topic of interest, including analyzing a first gyroscope sensor data and a second gyroscope sensor data to determine an impact point or release point;
selecting, from a content database, content associated with the topic; and
displaying the selected content on the mobile device.

11. A system, comprising:
a server;
a content database linked to the server;
a dynamic lesson generator and
a plurality of mobile devices linked to the server, each of the mobile devices having motion sensors integrated therein;
wherein when one of the mobile devices is held in a hand and moved using the hand to simulate a sports motion, the sports motion is evaluated to determine at least one topic;
a presentation snippet is assembled from content retrieved from the content database, the presentation snippet relating to the topic; and
the presentation snippet is displayed;
wherein the evaluation of the sports motion to determine the at least one topic comprises:
obtaining motion data from one or more of the motion sensors;
using the obtained motion data, determining the starting point, velocity of an impact point around a virtual object or release point of a virtual object and movement along a path.

12. The system of claim 11, wherein a plurality of the mobile devices are linked to the server concurrently simulating the same sport.

13. The system of claim 11, wherein a first one of the mobile devices is used to simulate a first sport and a second one of the mobile devices is used to simulate a second sport, the first one of the mobile devices and the second one of the mobile devices linked to the server concurrently.

14. The system of claim 11, wherein the presentation snippet is displayed on the same mobile device used to simulate the sports motion.

15. The system of claim 11, wherein the presentation snippet is displayed on a display device different from the mobile device used to simulate the sports motion.

16. The system of claim 11, wherein the presentation snippet includes a sports lesson.

17. The system of claim 11, wherein the presentation snippet includes video.

18. The system of claim 11, wherein the presentation snippet includes text.

19. The system of claim 11, wherein the presentation snippet includes audio.

20. The system of claim 11, wherein the presentation snippet includes an animation.

21. The system of claim 11, wherein the mobile devices are linked to the server via the Internet.

22. The system of claim 11, wherein the sports motion relates to a sport impacting an object.

23. The system of claim 22, wherein the sport is one of golf, baseball, tennis, badminton, racquetball, table tennis, and hockey.

24. The system of claim 11, wherein the sports motion relates to releasing an object.

25. The system of claim 24, wherein the sport is one of bowling, baseball, basketball, American football, bean bag toss, and fly fishing.

26. The system of claim 11, wherein the motion sensors include a gyroscope and an accelerometer.

27. The system of claim 11, wherein the evaluation of the movement includes evaluating pitch, roll, and yaw of the mobile device.

28. The system of claim 11, further comprising a database for storing motion data related to motions of the mobile device during the simulated sports motion.

29. The system of claim 11, wherein the presentation snippet is assembled by obtaining content based on one or more of user input data, prior motion data, CRM data, and assembling the obtained content, according to a set of predetermined rules.

30. The system of claim 11, wherein the presentation snippet is displayed on a web-enabled display device separate and distinct from the mobile device.

31. The system of claim 30, wherein the presentation snippet which is displayed on a web-enabled display device includes a virtual target to be impacted with a virtual object, responsive to the sports motion.

32. A method of analyzing sports motions, comprising:
(a) determining a starting point of a sports motion to be simulated using a mobile device having integrated motion sensors, wherein the starting point is indicated by the mobile device being held still for a predetermined length of time;
(b) using a hand, moving the mobile device from the starting point along a path to complete the simulation;

(c) obtaining motion data from the motion sensors relating to the starting point and the movement along the path;

(d) determining an occurrence of a simulated sports event using the obtained motion data;

(e) evaluating the simulated sports motion to determine at least one topic of interest, wherein evaluation of the sports motion includes use of longitudinal data for measuring performance improvement;

(f) selecting, from a content database, content associated with the topic;

(g) displaying the selected content; and (h) determining a velocity of a virtual object around an impact point or a release point, wherein the sports event is an impact point with, or a release point of, a virtual object, wherein determining the velocity does not use data from an accelerometer.

33. The method of claim 32, wherein the content is displayed on the mobile device.

34. The method of claim 32, wherein the content is displayed on a display device different from the mobile device.

35. The method of claim 32, wherein the mobile device is not attached to any piece of sports equipment and the starting point is not indicated by user-entered input.

36. The method of claim 32, wherein the motion sensors include the accelerometer and a multi-axis gyroscope.

37. The method of claim 32, wherein the virtual object is one of a virtual golf ball, a basketball, an American football, a baseball, a tennis ball, a shuttlecock, a racquetball, a lacrosse ball, a table tennis ball, and a hockey puck.

38. The method of claim 32, wherein determining the velocity is based at least in part on velocity of the mobile device around the impact point, arm length, club length, and arc length for a swing type.

39. The method of claim 32, wherein determining the velocity includes applying a multiplier based on estimated wrist hinge and forearm rotation as measured by yaw and roll of the mobile device at the impact point.

40. The method of claim 32, further including determining ball flight distance based at least in part on the determined velocity of the virtual object.

41. The method of claim 32, wherein determining the occurrence of the simulated sports event using the obtained motion data includes analyzing a first gyroscope sensor data of the mobile device during the simulated sports motion to determine the impact point or release point.

42. The method of claim 32, wherein determining the occurrence of the simulated sports event using the obtained motion data includes analyzing a second gyroscope sensor data of the mobile device at the impact point.

43. The method of claim 32, wherein analyzing a second sensor of the mobile device at the impact point includes subtracting sensor data at the impact point from sensor data from the starting point.

44. The method of claim 32, wherein the release point is one of a release point of a bowling ball, a lacrosse handle, a basketball, a baseball, a hockey stick, a bean bag, an American football and a fishing rod.

45. The method of claim 32, further comprising storing motion data related to motions of the mobile device during the simulated sports motion in a database.

46. The method of claim 32, wherein the presentation snippet is assembled by obtaining content based on one or more of user input data, prior motion data, and CRM data, and assembling the obtained content, according to a set of predetermined rules.

47. The method of claim 1, wherein the selected content is further displayed on a display device different from the mobile device used to simulate the sports motion.

48. The apparatus of claim 10, wherein the motion sensors include a gyroscope and an accelerometer.

49. The apparatus of claim 10, wherein the step of evaluating the simulated sports motions by the processor includes evaluating pitch, roll, and yaw of the mobile device.

50. The apparatus of claim 10, wherein the mobile device includes a phone.

51. The apparatus of claim 10, wherein the selected content includes a video clip of an instructor providing motion improvement information.

52. The apparatus of claim 10, wherein the processor is integral to the mobile device.

53. The apparatus of claim 10, wherein the processor performs the steps when the mobile device is held by a user while being moved.

54. The apparatus of claim 10, wherein the processor further stores motion data related to motions of the mobile device during the simulated sports motion in a database.

55. The apparatus of claim 10, wherein selecting the content by the processor includes obtaining content based on one or more of user input data, prior motion data, and CRM data, and assembling the obtained content, the selecting and assembling according to a set of predetermined rules.

56. The apparatus of claim 10, wherein the selected content is further displayed on a display device different from the mobile device used to simulate the sports motion.

* * * * *